United States Patent [19]

Lunts

[11] Patent Number: 4,937,251
[45] Date of Patent: * Jun. 26, 1990

[54] DICHLOROANILINE COMPOUNDS USEFUL FOR METHOD OF THERAPY OR PROPHYLAXIS OF A DISEASE ASSOCIATED WITH REVERSIBLE AIRWAY OBSTRUCTION

[75] Inventor: Lawrence H. C. Lunts, Broxbourne, England

[73] Assignee: Glaxo Group Limited, London, England

[ * ] Notice: The portion of the term of this patent subsequent to May 1, 2007 has been disclaimed.

[21] Appl. No.: 13,895

[22] Filed: Feb. 11, 1987

[30] Foreign Application Priority Data

Feb. 12, 1986 [GB] United Kingdom ................ 8603475

[51] Int. Cl.$^5$ ............................................ A61K 31/44
[52] U.S. Cl. ..................... 514/351; 514/348; 514/357; 546/296; 546/300; 546/334
[58] Field of Search ............... 546/296, 300, 303, 334, 546/290; 514/348, 351, 357, 345

[56] References Cited

U.S. PATENT DOCUMENTS 4,379,166  4/1983  Neustadt ............................. 546/176

FOREIGN PATENT DOCUMENTS

| 21636 | 1/1981 | European Pat. Off. ............ 546/300 |
| 0219350 | 4/1987 | European Pat. Off. ............ 546/334 |
| 3434271 | 3/1986 | Fed. Rep. of Germany ...... 546/121 |
| 1178191 | 1/1970 | United Kingdom ................ 546/300 |
| 1445740 | 8/1976 | United Kingdom ................ 546/334 |
| 1599061 | 9/1981 | United Kingdom ................ 546/176 |
| 2088873 | 6/1982 | United Kingdom ................ 546/300 |

Primary Examiner—Richard A. Schwartz
Assistant Examiner—Zinna Northington-Davis

[57] ABSTRACT

The invention provides compounds of the general formula (I)

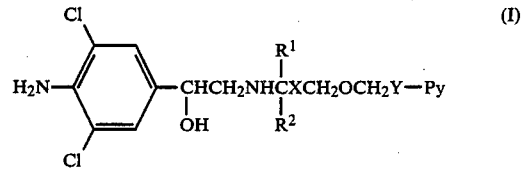

wherein
X represents a bond or a $C_{1-6}$ alkylene, $C_{2-6}$ alkenylene or $C_{2-6}$ alkynylene chain, and
Y represents a bond, or a $C_{1-4}$ alkylene, $C_{2-4}$ alkenylene or $C_{2-4}$ alkynylene chain with the proviso that the sum total of carbon atoms in X and Y is not more than 8;
Py represents a pyridyl group optionally substituted by one or two substituents selected from halogen atoms, hydroxy, $C_{1-3}$ alkyl and $C_{1-3}$ alkoxy groups; and
$R^1$ and $R^2$ each represent a hydrogen atom or a $C_{1-3}$ alkyl group, with the proviso that the sum total of carbon atoms in $R^1$ and $R^2$ is not more than 4; and physiologically acceptable salts and solvates (e.g. hydrates) thereof.

The compounds have a stimulant action at $\beta_2$-adrenoreceptors and may be used in the treatment of diseases associated with reversible airways obstruction such as asthma and chronic bronchitis.

12 Claims, No Drawings

DICHLOROANILINE COMPOUNDS USEFUL FOR METHOD OF THERAPY OR PROPHYLAXIS OF A DISEASE ASSOCIATED WITH REVERSIBLE AIRWAY OBSTRUCTION

This invention relates to dichloroaniline derivatives having a stimulant action at $\beta_2$-adrenoreceptors, to processes for their preparation, to pharmaceutical compositions containing them and to their use in medicine.

Dihaloaniline derivatives have previously been described as bronchodilators having stimulant activity at $\beta$-adrenoreceptors.

Thus British Patent Specification No. 1178191 describes compounds of the general structure

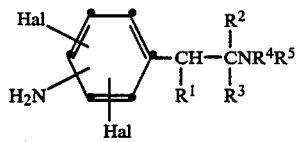

in which the substituents Hal represent bromine or chlorine atoms; $R^1$ represents hydrogen or hydroxyl; $R^2$ and $R^3$ each represent hydrogen or $C_{1-4}$ alkyl; and $R^4$ and $R^5$ each represent hydrogen, $C_{1-6}$ alkyl, alkenyl, alkynyl, hydroxyalkyl, alkoxyalkyl, dialkylaminoalkyl, cycloalkyl, phenyl, benzyl or adamantyl, or $NR^4R^5$ forms a heterocylic ring optionally substituted by $C_{1-3}$ alkyl groups.

We have now found a novel group of dichloroaniline derivatives, which differ structurally from those described in British Patent Specification No. 1178191, and which have a desirable and useful profile of activity.

Thus the present invention provides compounds of the general formula (I)

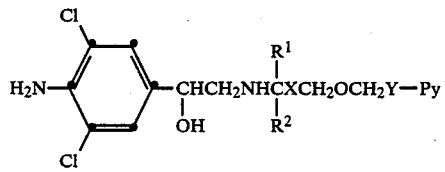

wherein

X represents a bond or a $C_{1-6}$ alkylene, $C_{2-6}$ alkenylene or $C_{2-6}$ alkynylene chain and Y represents a bond, or a $C_{1-4}$ alkylene, $C_{2-4}$ alkenylene or $C_{2-4}$ alkynylene chain with the proviso that the sum total of carbon atoms in X and Y is not more than 8;

Py represents a pyridyl group optionally substituted by one or two substituents selected from halogen atoms or hydroxy, $C_{1-3}$ alkyl or $C_{1-3}$ alkoxy groups; and $R^1$ and $R^2$ each represent a hydrogen atom or a $C_{1-3}$ alkyl group, with the proviso that the sum total of carbon atoms in $R^1$ and $R^2$ is not more than 4; and physiologically acceptable salts and solvates (e.g. hydrates) thereof.

It will be appreciated that the compounds of general formula (I) possess one or two asymmetric carbon atoms, namely the carbon atom of the

group and, when $R^1$ and $R^2$ are different groups, the carbon atom to which these are attached. The compounds according to the invention thus include all enantiomers, diastereoisomers and mixtures thereof, including racemates. Compounds in which the carbon atom in the

group is in the R configuration are preferred.

In the definition of general formula (I), the term alkenylene includes both cis and trans structures.

In one aspect the invention provides compounds of formula (I) in which $R^1$, $R^2$, Y and Py are as defined in formula (I), and X represents a $C_{1-6}$ alkylene, $C_{2-6}$ alkenylene or $C_{2-6}$ alkynylene claim.

In the general formula (I), the chain X may be for example $-(CH_2)_2-$, $-(CH_2)_3-$, $-(CH_2)_4-$, $-(CH_2)_5-$, $-(CH_2)_6-$, $-CH_2C\equiv C-$, $-(CH_2)_2CH=CH-$, $-(CH_2)_2C\equiv C-$, $-CH=CHCH_2-$, $-CH=CH(CH_2)_2-$ or $-CH_2C\equiv CCH_2-$.

The chain Y may be for example $-CH_2-$, $-(CH_2)_2-$, $-(CH_2)_3-$, $-(CH_2)_4-$, $-CH=CH-$, $-C\equiv C-$, $CH_2CH=CH-$ or $-CH_2C\equiv C-$. Y may also represent for example a bond.

Preferably the total number of carbon atoms in the chains X and Y is 4 to 8 inclusive. Compounds wherein the sum total of carbon atoms in the chains X and Y is 4, 5, 6 or 7 are particularly preferred.

In one preferred group of compounds of formula (I) X represents a $C_{2-6}$ alkynylene or, more preferably, a $C_{1-6}$ alkylene chain and Y represents a $C_{1-4}$ alkylene chain. Particular compounds of this type are those wherein X is $-(CH_2)_3-$ or $-(CH_2)_4-$ and Y is $-CH_2-$, $-(CH_2)_2-$ or $-(CH_2)_3-$, or X is $-(CH_2)_2C\equiv C-$ and Y is $-(CH_2)_2-$.

In the compounds of formula (I) $R^1$ and $R^2$ may each be, for example, methyl, ethyl, propyl or isopropyl groups except that if one of $R^1$ and $R^2$ is a propyl or isopropyl group, the other is a hydrogen atom or a methyl group. $R^1$ and $R^2$ are each preferably a hydrogen atom or a methyl group.

A preferred group of compounds are those wherein $R^1$ and $R^2$ are both hydrogen atoms, or $R^1$ is a hydrogen atom and $R^2$ is a $C_{1-3}$ alkyl group, particularly a methyl group.

The pyridyl group represented by Py may be attached to the rest of the molecule at either the 2-, 3- or 4-position.

When the pyridyl group is substituted, the substituent(s) may be at the 2-, 3-, 4-, 5- or 6-position(s) in the ring. When the pyridyl group is substituted by one or two halogen atoms, these may be fluorine, chlorine or, more preferably, bromine. When the pyridyl group Py is substituted, it preferably contains a single substituent. More preferably the substituted pyridyl group is attached to the rest of the molecule at the 2-position, and the single substituent is at the 3-, 5- or 6-position.

A preferred group of compounds are those of formula (I) in which $R^1$ represents a hydrogen atom and $R^2$ represents a hydrogen atom or a $C_{1-3}$ alkyl (e.g. methyl)group, X represents $-(CH_2)_3-$, $-(CH_2)_4-$ or $-(CH_2)_2C\equiv C-$, Y represents $-CH_2-$, $-(CH_2)_2-$ or $-(CH_2)_3-$, and Py represents a pyridyl group attached to the rest of the molecule at the 2-, 3- or 4-position, optionally containing a single substituent selected from hydroxy, $C_{1-3}$ alkyl (e.g. methyl), $C_{1-3}$ alkoxy (e.g. methoxy) or halogen (e.g. bromine).

A further preferred group of compounds are those of formula (I) in which $R^1$ represents a hydrogen atom and $R^2$ represents a hydrogen atom or a methyl group, X represents $-(CH_2)_4-$ or $-(CH_2)_2C\equiv C-$, Y represents $-CH_2-$, $-(CH_2)_2-$ or $-(CH_2)_3-$, and Py represents a pyridyl group attached to the rest of the molecule at the 2-, 3- or 4-position, optionally containing a single substituent selected from hydroxy or methyl.

A particularly preferred group of compounds are those of formula (I) in which $R^1$ and $R^2$ both represent hydrogen atoms, X represents $-(CH_2)_4-$, Y represents $-CH_2-$, $-(CH_2)_2-$ or $-(CH_2)_3-$, and Py represents an unsubstituted pyridyl group attached to the rest of the molecule at the 2- or 3-position, or a 2-pyridyl group containing a single hydroxy substituent.

Especially preferred compounds from within this group are those in which Py is an unsubstituted pyridyl group attached to the rest of the molecule at the 2-position.

Particularly preferred compounds according to the invention are:

4-amino-3,5-dichloro-α-[[[6-[2-(2-pyridinyl)ethoxy]hexyl]amino]methyl]benzenemethanol;

4-amino-3,5-dichloro-α-[[[6-[3-(3-pyridinyl)propoxy]hexyl]amino]methyl]benzenemethanol;

4-amino-3,5-dichloro-α-[[[6-[4-(3-hydroxy-2-pyridinyl)butoxy]hexyl]amino]methyl]benzenemethanol;

4-amino-3,5-dichloro-α-[[[6-[3-(2-pyridinyl)propoxy]hexyl]amino]methyl]benzenemethanol;

4-amino-3,5-dichloro-α-[[[6-[2-(3-pyridinyl)ethoxy]hexyl]amino]methyl]benzenemethanol;

4-amino-3,5-dichloro-α-[[[1-methyl-6-[2-(2-pyridinyl)ethoxy]hexyl]amino]methyl]benzenemethanol;

and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, tricarballylates, hydroxynaphthalenecarboxylates e.g. 1-hydroxy- or 3-hydroxy-2-naphthalenecarboxylates, or oleates.

The compounds according to the invention have a stimulant action at $\beta_2$-adrenoreceptors, which furthermore is of a particularly advantageous profile. The stimulant action was demonstrated in the isolated trachea of the guinea-pig, where compounds were shown to cause relaxation of contractions induced by $PGF_{2\alpha}$- or electrical stimulation. Compounds according to the invention have shown a particularly long duration of action in these tests.

The compounds according to the invention may be used in the treatment of diseases associated with reversible airways obstruction such as asthma and chronic bronchitis.

The compounds according to the invention are also indicated as useful for the treatment of inflammatory and allergic skin diseases, congestive heart failure, depression, premature labour, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multidose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes, as described in the following, wherein X, Y, Py, $R^1$ and $R^2$ are as defined for general formula (I) unless otherwise specified. In addition, the pyridyl group Py may be as defined in formula (I) or may be in a form which is subsequently convertible into the required grouping by conventional methods.

It will be appreciated that certain of the reactions described below are capable of affecting other groups in the starting material which are desired in the end product; this applies especially in the reduction processes described, particularly where hydrogen and a catalyst are used and when an ethylene or acetylene linkage is required in the compound of the invention. Care must therefore be taken in accordance with conventional practice, either to use reagents which will not affect such groups, or to perform the reaction as part of a sequence which avoids their use when such groups are present in the starting material.

In the preparation of both intermediates and end-products the final step in the reaction may be the removal of a protecting group. Conventional protecting groups may be used, as described for example in "Protective Groups in Organic Chemistry", by Theodora Greene (John Wiley and Sons Inc, 1981). Thus hydroxyl groups may for example be protected by arylmethyl groups such as benzyl, diphenylmethyl or triphenylmethyl, by acyl groups such as acetyl, or as tetrahydropyranyl derivatives. Suitable amino protecting groups include arylmethyl groups such as benzyl, α-methylbenzyl, diphenylmethyl or triphenylmethyl, and acyl groups such as acetyl, trichloroacetyl or trifluoroacetyl.

Conventional methods of deprotection may be used. Thus for example arylmethyl groups may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with an acid such as a mineral acid e.g. hydrochloric acid, or a base such as sodium hydroxide or potassium carbonate, and a group such as trichloroacetyl may be removed by reduction with, for example, zinc and acetic acid.

In one general process (1), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (II)

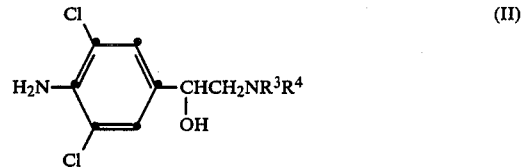

(wherein $R^3$ is a hydrogen atom or a protecting group and $R^4$ is a hydrogen atom) followed by removal of any protecting group where present.

The alkylation (a) may be effected using an alkylating agent of general formula (III):

(wherein L is a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform, at a temperature between ambient and the reflux temperature of the solvent.

According to another example (b) of an alkylation process, a compound of general formula (I) in which $R^1$ represents a hydrogen atom may be prepared by alkylation of an amine of general formula (II), as previously defined except that $R^4$ is a hydrogen atom or a group convertible thereto under the reaction conditions, with a compound of general formula (IV):

in the presence of a reducing agent, followed when necessary by removal of any protecting groups.

Examples of suitable $R^4$ groups convertible into a hydrogen atom are arylmethyl groups such as benzyl, α-methylbenzyl and benzhydryl.

Suitable reducing agents include hydrogen in the presence of a catalyst such as platinum, platinum oxide, palladium, palladium oxide, Raney nickel or rhodium, on a support such as charcoal, using an alcohol, e.g. ethanol or methanol, or an ester e.g. ethyl acetate, or an ether e.g. tetrahydrofuran, or water, as reaction solvent, or a mixture of solvents, e.g. a mixture of two or more of those just described at normal or elevated temperature and pressure, for example from 20° to 100° C. and from 1 to 10 atmospheres.

Alternatively when one or both of $R^3$ and $R^4$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (II) where $R^3$ and $R^4$ are each hydrogen atoms is used, the intermediate imine of formula (V) may be formed:

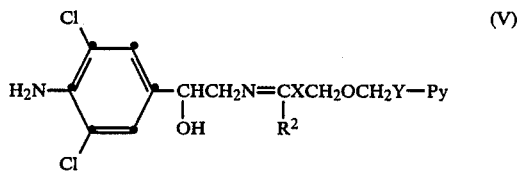

Reduction of the imine using the conditions described above, followed, where necessary, by removal of any protecting groups, gives a compound of general formula (I).

In another general process (2), a compound of general formula (I) may be prepared by reduction. Thus, for example, a compound of general formula (I) may be prepared by reducing an intermediate of general formula (VI):

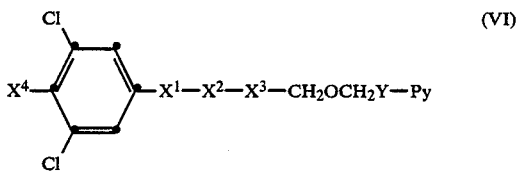

wherein at least one of $X^4$, $X^1$, $X^2$, $X^3$ and Y represents a reducible group and/or Py contains a reducible group and the other(s) take the appropriate meaning as follows, which is $X^4$ is —$NHR^6$, $X^1$ is —CH(OH)—, $X^2$ is —$CH_2NR^3$— (wherein $R^3$ and $R^6$ each represent a hydrogen atom or a protecting group), $X^3$ is —$CR^1R^2X$, and Py and Y are as defined in formula (I), followed where necessary by removal of any protecting groups.

Suitable reducible groups include those wherein $X^4$ is —$NO_2$, $X^1$ is a group

$X^2$ is a group —$CH_2NR^5$— (wherein $R^5$ represents a group convertible to hydrogen by catalytic hydrogenation, for example an arylmethyl group such as benzyl, benzhydryl or α-methylbenzyl) or an imine (—CH=N—) group or a group —CONH—, $X^3$ is a group —COX— or a group $CR^1R^2X$ (where X is $C_{2-6}$ alkenylene or $C_{2-6}$ alkynylene), or —$X^2$—$X^3$— is a group —$CH_2N$=$CR^2X$—, Y is $C_{2-4}$ alkenylene or alkynylene, and Py is a pyridyl N-oxide group.

The reduction may be effected using reducing agents conveniently employed for the reduction of ketones, imines, amides, protected amines, alkenes, alkynes, N-oxides and nitro groups.

Thus, for example, when $X^4$ in general formula (VI) represents a nitro group, this may be reduced to an amino group using hydrogen in the presence of a catalyst as previously described for process (1) part (b).

When $X^1$ in general formula (VI) represents a >C=O group this may be reduced to a —CH(OH)— group using hydrogen in the presence of a catalyst as previously described for process (1) part (b). Alternatively, the reducing agent may be, for example a hydride such as diborane or a metal hydride such as lithium aluminium hydride, sodium bis(2-methoxyethoxy) aluminium hydride, sodium borohydride or aluminium hydride. The reaction may be effected in a solvent, where appropriate an alcohol e.g. methanol or ethanol, or an ether such as tetrahydrofuran, or a halogenated hydrocarbon such as dichloromethane.

When $X^2$ in general formula (VI) represents a —$CH_2R^5$— group or the group CH=N—, or —$X^2$—$X^3$— represents —$CH_2N$=$CR^2X$— this may be reduced to a —$CH_2NH$— or —$CH_2NHCHR^2X$— group using hydrogen in the presence of a catalyst as previously described for process (1) part (b). Alternatively, when $X^2$ or —$X^2$—$X^3$— is the group —CH=N— or —$CH_2N$=$CR^2X$— this may be reduced to a —$CH_2NH$— or —$CH_2NHCHR^2X$— group using a reducing agent and conditions as just described for the reduction of $X^1$ when this represents a >C=O group.

When $X^2$ or $X^3$ in general formula (VI) represents a —CONH— or —COX— group, this may be reduced to a group —$CH_2NH$— or —$CH_2X$—, using a hydride such as diborane or a complex metal hydride such as lithium aluminium hydride or sodium bis(2-methoxyethoxy)aluminium hydride in a solvent such as an ether, e.g. tetrahydrofuran or diethyl ether.

When $X^3$ represents a group $CR^1R^2X$ where X is $C_{2-6}$ alkenylene or $C_{2-6}$ alkynylene, or Y represents $C_{2-4}$ alkenylene or $C_{2-4}$ alkynylene, this may be reduced to $C_{2-6}$ alkylene or $C_{2-4}$ alkylene respectively using hydrogen in the presence of a catalyst as previously described for process (1) part (b). Alternatively, when X is $C_{2-6}$ alkynylene or Y is $C_{2-4}$ alkynylene this may be reduced to $C_{2-6}$ alkenylene or $C_{2-4}$ alkenylene respectively using for example hydrogen and a lead-poisoned palladium on calcium carbonate catalyst in a solvent such as pyridine, or lithium aluminium hydride in a solvent such as diethyl ether at a low temperature e.g. 0° C.

When Py represents a pyridyl N-oxide group, this may be reduced to a pyridyl group using hydrogen and a catalyst such as Raney nickel, in a solvent such as an alcohol e.g. methanol.

Where it is desired, in the above processes (1b) and (2), to use a protected intermediate of general formula (II) or (VII), it is particularly convenient to use a protecting group $R^3$ and/or $R^6$ which is capable of being removed under the reducing conditions, for example hydrogen and a catalyst, thus avoiding the need for a separate deprotection step. Suitable protecting groups include arylmethyl groups such as benzyl, benzhydryl and α-methylbenzyl.

In a further general process (3), a compound of general formula (I) may be prepared by deprotection of a protected intermediate of formula (VII)

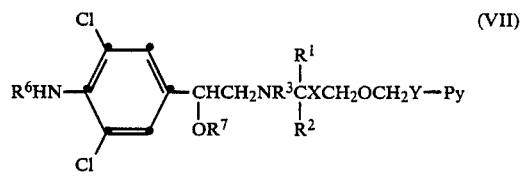

where $R^3$, $R^6$ and $R^7$ each represent a hydrogen atom or a protecting group, or $R^3$ and $R^7$ together represent a protecting group, and/or any hydroxy substituent in the group Py is protected, with the proviso that at least one of $R^3$, $R^6$ and/or $R^7$ represents a protecting group and/or Py contains a protecting group.

Conventional protecting groups and methods for their removal may be used, as described previously. Thus, for example, $R^3$ may represent an arylmethyl group e.g. benzyl, which may be removed by hydrogenolysis in the presence of a metal catalyst (e.g. palladium on charcoal), and/or $R^3$, $R^6$ and/or $R^7$ may represent an acyl (e.g. acetyl) group(s) which may be removed by boiling with a dilute mineral acid (e.g. hydrochloric acid), or treating with a base (e.g. sodium hydroxide) in a solvent such as an alcohol (e.g. ethanol) at room temperature.

In a further embodiment of the deprotection process (3) the groups $R^3$ and $R^7$ may together represent a protecting group as in a compound of formula (VIII)

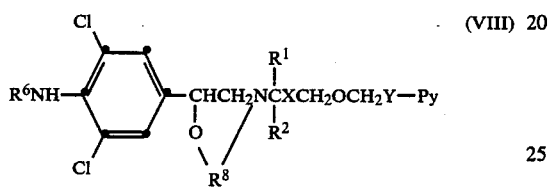

(VIII)

where $R^6$ represents a hydrogen atom or a protecting group, Py may contain a protecting group and $R^8$ represents a carbonyl or thiocarbonyl moiety or a group $CR^{10}R^{11}$ (where $R^{10}$ and $R^{11}$ each represent a hydrogen atom or an alkyl group, or one or $R^{10}$ and $R^{11}$ may represent an aryl e.g. phenyl group) formed from an aldehyde or ketone such as acetaldehyde or acetone. A compound of formula (VIII) may be converted into a compound or formula (I) by hydrolysis under acidic or basic conditions using for example aqueous hydrochloric or sulphuric acid or sodium hydroxide, with, where necessary, removal of any other protecting groups using the methods described above. The hydrolysis may conveniently be carried out in a solvent such as an ether (e.g. tetahydrofuran) at a temperature of for example room temperature to 100° C.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid in the presence of a suitable solvent such as acetonitrile, acetone, chloroform, ethyl acetate or an alcohol, e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

Intermediates of formula (VI) for use in the reduction process (2) may be prepared by a number of processes, analogous to those described in UK Patent Specification No. 2165542A.

Thus for example intermediates of formula (VI) in which $X^1$ is the group

may be prepared from a haloketone of formula (IX)

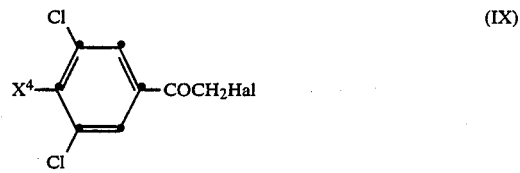

(where $X^4$ is as defined in formula (VI) and Hal represents a halogen atom e.g. bromine) by reaction with an amine of general formula (X)

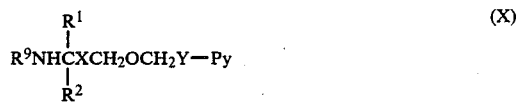

(X)

(where $R^9$ is a hydrogen atom or a group convertible thereto by catalytic hydrogenation). The reaction may be effected in a cold or hot solvent, for example tetrahydrofuran, tert-butyl methyl ether, dioxan, chloroform, dichloromethane, dimethylformamide, acetonitrile, a ketone such as butanone or methylisobutylketone, or an ester such as ethyl acetate, preferably in the presence of a base such as diisopropylethylamine, sodium carbonate or other acid scavenger such as propylene oxide.

Intermediates of general formula (VI) in which $X^1$ is a group

may be reduced to the corresponding intermediate in which $X^1$ is a group —CH(OH)— using for example a metal hydride such as sodium borohydride in a solvent e.g. ethanol, methanol and/or tetrahydrofuran.

The intermediate amines of formula (X), particularly those in which $R^1$ and $R^2$ both represent hydrogen atoms, and their acid addition salts are novel compounds and constitute a further aspect of the invention.

Intermediates of formula (VI) in which $X^2$ is the group —CH=N— may be prepared by reacting a glyoxal derivative of formula (XI)

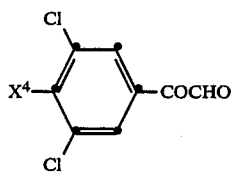

(XI)

(where $X^4$ is as defined in formula (VI)) with an amine of formula (X) (in which $R^9$ represents a hydrogen atom), in a solvent such as benzene, tetrahydrofuran or an alcohol e.g. ethanol at temperatures up to the reflux temperature of the solvent.

Intermediates of formula (VI) in which $X^3$ represents —COX— may be prepared by acylation of an amine of formula (XII)

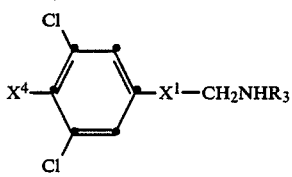

(XII)

(where $X^1$ and $X^4$ are as defined previously, and $R^3$ is a hydrogen atom) using an activated derivative of an acid of formula (XIII)

$$Py-YCH_2OCH_2XCO_2H \qquad (XIII)$$

Suitable activated derivatives include the imidazolide formed by reaction of the acid (XIII) with 1,1¹-carbonyldiimidazole. The acylation may be carried out in a solvent such as acetonitrile.

Intermediates of formula (VIII) may be prepared from compounds of formula (XIV)

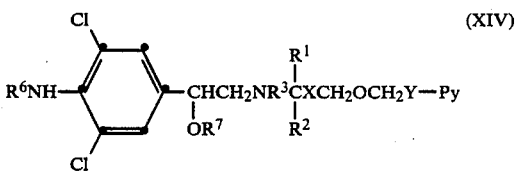

(XIV)

(where $R^6$ is as defined previously, and $R^3$ and $R^7$ are both hydrogen atoms) by reaction with 1,1¹-carbonyldiimidazole or 1,1¹-thiocarbonyldiimidazole.

The amines of general formula (X) in which $R^9$ is a group convertible to hydrogen and $R^1$ and $R^2$ are both hydrogen atoms may be prepared by reaction of a compound of general formula (III) in which $R^2$ is a hydrogen atom with an amine $R^9NH_2$. The reaction may be effected in the absence or presence of a solvent such as a ketone e.g. butanone or methyl isobutyl ketone, an ether e.g. tetrahydrofuran or a substituted amide e.g. dimethylformamide, optionally in the presence of a base such as sodium carbonate or an organic amine e.g. triethylamine or N,N-diisopropylethylamine at temperatures between 0° C. and the reflux temperature of the solvent. When the reaction is carried out in the absence of a solvent, the two reactants may be heated at temperatures up to for example 150° C. Where desired, subsequent reaction with hydrogen in the presence of metal catalyst such as platinum in a solvent such as an alcohol e.g. ethanol yields a compound of formula (X) where $R^9$ is a hydrogen atom.

Intermediates of formulae (II), (IX), (XI) and (XII) are either known compounds or may be prepared by methods analogous to those described for the preparation of known compounds.

Suitable methods for preparing intermediates of formulae (III), (IV), (X) and (XIII) are described in UK Patent Specification Nos. 2140800A, 2159151A and 2165542A and in the exemplification included hereinafter.

The following examples illustrate the invention. Temperatures are in °C. 'Dried' refers to drying using magnesium sulphate or sodium sulphate except where otherwise stated. Thin layer chromatography (t.l.c.) was carried out on SiO₂ and flash column chromatography (FCC) was carried out on silica (Merck 9385) using, unless otherwise stated, one of the following solvent systems: A-toluene:ethanol:0.88 ammonia; B-hexane:ethyl acetate:triethylamine; C-toluene:ethanol:triethylamine. The following abbreviations are used: THF - tetrahydrofuran; DMF - dimethylformamide; BTPC - bis(triphenylphosphine) palladium (II) chloride; DEA - N,N-diisopropylethylamine; DMSO-dimethylsulphoxide; TAB - tetra-n-butylammonium bisulphate.

Intermediate 1 is
1-(4-amino-3,5-dichlorophenyl)-2-bromoethanone.

Intermediate 2 is
4-amino-α-(aminomethyl)-3,5-dichlorobenzenemethanol.

Intermediate 3

N-[6-[[3-(2-Pyridinyl)-2-propynyl]oxy]hexyl]benzenemethanamine

A mixture of 2-bromopyridine (2.0 g), N-[6-[(2-propynyl)oxy]hexyl]benzenemethanamine (3.2 g), BTPC (0.07 g), cuprous iodide (0.007 g), and diethylamine (20 ml) was stirred under nitrogen for 18 h, treated with aqueous sodium bicarbonate (1M, 50 ml), and extracted with diethyl ether (2×100 ml). The dried extract was evaporated and the residue was purified by FCC eluting with diethyl ether to give the *title compound* as a yellow oil (3.0 g), t.l.c. (diethyl ether) Rf 0.05.

Intermediate 4

2-[2-[(6-Bromohexyl)oxy]ethyl]pyridine

A mixture of 2-pyridineethanol (5 g), 1,6-dibromohexane (20 ml), 50% (w/v) sodium hydroxide (20 ml) and TAB (500 mg) was stirred at room temperature for 6 h. Water (100 ml) was added and the mixture was extracted with ether (2×100 ml). The organic extracts were washed with water and brine, dried and concentrated to an oil which was purified by FCC eluting with hexane→hexane-ether (1:1) to give the *title compound* as a colourless oil (6.6 g), t.l.c. (hexane-ether 1:1) Rf 0.19.

Intermediates 5-14 were prepared in a similar manner from the appropriate alcohol and bromocompound:

Intermediate 5

3-[3-[(6-Bromohexyl)oxy]propyl]pyridine as a yellow oil (11.0 g), t.l.c. (hexane-ether 1:1) Rf 0.16, from 3-pyridinepropanol (10 g) and 1,6-dibromohexane (40 ml) with a reaction time of 3 h.

Intermediate 6

(Z)-2-[4-[(6-Bromohexyl)oxy]-1-butenyl]-3-(phenylmethoxy)pyridine

From (E/Z)-4-[3-(phenylmethoxy)-2-pyridinyl]-3-buten-1-ol (2.74 g) and 1,6-dibromohexane (10.03 g), with a reaction time of 18 h and using ethyl acetate for extraction. FCC eluting with cyclohexane-ethyl acetate (100:0→95:5) gave the *title compound* as a yellow oil (1.74 g), t.l.c. (ethyl acetate-cyclohexane 5:95) Rf 0.17.

Intermediate 7

2-[2-[(6-Bromohexyl)oxy]ethyl]-6-methylpyridine

From 6-methyl-2-pyridineethanol (5 g) and 1,6-dibromohexane (26 g), stirring the reaction mixture under nitrogen for 18 h, and using ethyl acetate for extraction. FCC eluting with cyclohexane→cyclohexane-ethyl acetate (92:8) gave the *title compound* as a yellow oil (9 g), t.l.c. (System A 80:20:1) Rf 0.6.

Intermediate 8

2-[3-[(2-Propynyl)oxy]propyl]pyridine

From 2-pyridinepropanol (13.7 g) and propargyl bromide (80% solution in toluene, 12 ml), with a reaction time of 2 h. FCC eluting with hexane-ether (1:1) gave the *title compound* as an orange oil (9.0 g), t.l.c. (System B 80:20:1) Rf 0.15.

Intermediate 9

4-[3-[(6-Bromohexyl)oxy]propyl]pyridine

From 4-pyridinepropanol (2.0 g) and 1,6-dibromohexane (8 ml), with a reaction time of 30 min. FCC eluting with hexane→ether gave the *title compound* as a colourless oil (1.1 g), t.l.c. (ether) Rf 0.45.

Intermediate 10

2-[3-[(5-Bromopentyl)oxy]propyl]pyridine

From 2-pyridinepropanol (5 g) and 1,5-dibromopentane (24.83 g), stirring the reaction mixture under nitrogen for 5 h, and using ethyl acetate for extraction. FCC eluting with cyclohexane→cyclohexane-ethyl acetate (9:1) gave the *title compound* as a yellow oil (5.5 g), t.l.c. (cyclohexane-ethyl acetate 9:1) Rf 0.15.

Intermediate 11

2-[4-[(6-Bromohexyl)oxy]butyl]pyridine

From 2-pyridinebutanol (3.96 g) and 1,6-dibromohexane (15 ml), with a reaction time of 4 h. FCC eluting with hexane→ether gave the *title compound* as a pale yellow oil (3.7 g), t.l.c. (hexane-diethyl ether 1:1) Rf 0.22.

Intermediate 12

2-[2-[(5-Bromopentyl)oxy]ethyl]pyridine

From 2-pyridineethanol (5.0 g) and 1,5-dibromopentane (16.6 ml), with a reaction time of 4 h. FCC eluting with hexane-diethyl ether (1:0→1:1) gave the *title compound* as a colourless oil (6.15 g), t.l.c. (ether-hexane 1:1) Rf 0.19.

Intermediate 13

2-[3-[(6-Bromohexyl)oxy]propyl]-5-bromopyridine

From 3-(5-bromo-2-pyridinyl)propanol (2 g) and 1,6-dibromohexane (6.77 g) with a reaction time of 3 h. FCC eluting with hexane→hexane:ether (100:0→90:10) gave the *title compound* as a yellow oil (2.4 g), t.l.c. (hexane:ether 9:1) Rf 0.08.

Intermediate 14

2-[2-[(4-Bromobutyl)oxy]ethyl]pyridine

From 2-pyridineethanol (5.0 g) and 1,4-dibromobutane (26.29 g), with a reaction time of 4 h. FCC eluting with ether-hexane (1:1) gave the *title compound* as a pale yellow oil (6.4 g), t.l.c. (ether-hexane 1:1) Rf 0.37.

Intermediate 15

N-[6-[2-(2-Pyridinyl)ethoxy]hexyl]benzenemethanamine

2-[2-[(6-Bromohexyl)oxy]ethyl]pyridine (6.3 g) was added to benzylamine (20 ml) at 140° under nitrogen. After 1 h at 140° the reaction mixture was cooled and partitioned between 2M sodium hydroxide (100 ml) and ether (100 ml). The organic layer was washed with water and brine, dried and concentrated to a yellow oil. The excess benzylamine was removed by distillation under reduced pressure to leave the *title compound* as a yellow oil (6.8 g) t.l.c. (System A 80:20:2) Rf 0.44.

Intermediates 16–22 were prepared in a similar manner by treating the appropriate bromocompound with benzylamine:

Intermediate 16

N-[6-[3-(3-Pyridinyl)propoxy]hexyl]benzenemethanamine as a yellow oil (7.5 g), t.l.c. (System A 80:20:2) Rf 0.41, from 3-[3-[(6-bromohexyl)oxy]propyl]pyridine (7.6 g) and benzylamine (24 ml).

Intermediate 17

N-[6-[4-(3-Hydroxy-2-pyridinyl)butoxy]hexyl]benzenemethanamine

From 2-[4-[(6-bromohexyl)oxy]butyl]-3-hydroxypyridine (1 g) and benzylamine (3 ml), partitioning the reaction mixture, after 4 h, between 8% sodium bicarbonate (10 ml) and ethyl acetate (10 ml). The final product was purified by FCC eluting with System C (95:5:1) to give the *title compound* as a yellow oil (0.8 g), t.l.c. (System C 95:5:1) Rf 0.25.

Intermediate 18

N-[6-[2-(6-Methyl-2-pyridinyl)ethoxy]hexyl]benzenemethanamine

From 2-[2-[(6-bromohexyl)oxy]ethyl]-6-methylpyridine (5 g) and benzylamine (15 ml), partitioning the reaction mixture between 8% sodium bicarbonate (50 ml) and ethyl acetate (50 ml). The final product was purified by FCC eluting with System C (95:5:1) to give the *title compound* as a pale yellow oil (3.7 g), t.l.c. (System C 95:5:1) Rf 0.32.

Intermediate 19

N-[6-[3-(4-Pyridinyl)propoxy]hexyl]benzenemethanamine

From 4-[3-[(6-bromohexyl)oxy]propyl]pyridine (1.1 g) and benzylamine (4 ml), partitioning the reaction mixture, after 30 min, between 8% sodium bicarbonate (15 ml) and ethyl acetate (20 ml). The final product was purified by FCC eluting with System C (95:5:1) to give the *title compound* as a yellow oil (1.0 g), t.l.c. (System C 90:10:1) Rf 0.22.

Intermediate 20

N-[5-[3-(2-Pyridinyl)propoxy]pentyl]benzenemethanamine

From 2-[3-[(5-bromopentyl)oxy]propyl]pyridine (6 g) and benzylamine (18 ml), partitioning the reaction mixture between 8% sodium bicarbonate (50 ml) and ethyl acetate (50 ml). The final product was purified by FCC eluting with System C (95:5:1) to give the *title compound* as a yellow oil (6 g), t.l.c. (System A 80:20:2) Rf 0.6.

Intermediate 21

N-[6-[4-(2-Pyridinyl)butoxy]hexyl]benzenemethanamine

From 2-[4-[(6-bromohexyl)oxy]butyl]pyridine (3.2 g) and benzylamine (10 ml), partitioning the reaction mixture between 8% sodium bicarbonate (50 ml) and ether (50 ml). The final product was purified by FCC eluting with System C (95:5:1) to give the *title compound* as a pale yellow oil (2.1 g), t.l.c. (System A 80:20:2) Rf 0.50.

Intermediate 22

N-[5-[2-(2-Pyridinyl)ethoxy]pentyl]benzenemethanamine

From 2-[2-[(5-bromopentyl)oxy]ethyl]pyridine (6.04 g) and benzylamine (33 ml). After 1 h at 130° the reaction mixture was cooled and partitioned between ethyl acetate (400 ml) and 8% aqueous sodium bicarbonate (250 ml). The final product was purified by FCC eluting with ethyl acetate-triethylamine (100:1) to give the *title compound* as a pale yellow oil (4.18 g), t.l.c. (ethyl acetate+few drops triethylamine) Rf 0.14.

Intermediate 23

4-Amino-3,5-dichloro-α-[[(phenylmethyl)[6-[2-(2-pyridinyl)ethoxy]hexyl]amino]methyl]benzenemethanol A solution of Intermediate 1 (1.0 g), N-[6-[2-(2-pyridinyl)ethoxy]hexyl]benzenemethanamine (1.01 g) and DEA (460 mg) in THF (10 ml) was left at room temperature for 2 h. The resulting precipitate was removed by filtration, the solvent was evaporated and the residue, in methanol (10 ml), was cooled in an ice-bath and treated portionwise with sodium borohydride (300 mg) under nitrogen. After 30 min, the solution was brought to room temperature, stirred for a further 30 min then concentrated in vacuo to a pale yellow foam. The foam was partitioned between water (25 ml) and ethyl acetate (25 ml) and the organic layer was washed with brine, dried and concentrated to a yellow oil which was purified by FCC eluting with System B (50:50:1) to give the *title compound* as a pale yellow oil (1.15 g), t.l.c. (System B 50:50:1) Rf 0.26.

Intermediates 24–32 were prepared in a similar manner from Intermediate 1 and the appropriate amine, followed by reduction with sodium borohydride.

Intermediate 24

(Z)-4-Amino-3,5-dichloro-α-[[(phenylmethyl)[6-[[3-(2-pyridinyl)-2-propenyl]oxy]hexyl]amino]methyl]benzenemethanol From Intermediate 1 (0.6 g) and N-[6-[[3-(2-pyridinyl)prop-2-ynyl]oxy]hexyl]benzenemethanamine (0.68 g), with reaction times of 16 h for both stages, and using methanol (20 ml) and THF (5 ml) as solvent for the reduction. FCC eluting with cyclohexane-diethyl ether (1:1) gave the *title compound* as a pale yellow oil (0.7 g), t.l.c. (diethyl ether) Rf 0.5.

Intermediate 25

4-Amino-3,5-dichloro-α-[[(phenylmethyl)[6-[3-(3-pyridinyl)propoxy]hexyl]amino]methyl]benzenemethanol From Intermediate 1 (1.5 g) and N-[6-[3-(3-pyridinyl)propoxy]hexyl]benzenemethanamine (1.73 g), with reaction times of overnight and 2 h for the two stages. FCC eluting with System B (66:33:1→50:50:1) gave the *title compound* as a pale yellow oil (1.5 g), t.l.c. (System B 50:50:1) Rf 0.28.

Intermediate 26

4-Amino-3,5-dichloro-α-[[[6-[4-(3-hydroxy-2-pyridinyl)butoxy]hexyl](phenylmethyl)amino]methyl]benzenemethanol From Intermediate 1 (0.6 g) and N-[6-[4-(3-hydroxy-2-pyridinyl)butoxy]hexyl]benzenemethanamine (0.7 g), with reaction times of 18 h and 2.5 h for the two stages. FCC eluting with System C (95:5:1) gave the *title compound* as a brown oil (0.6 g), t.l.c. (System A 80:20:1) Rf 0.25.

Intermediate 27

4-Amino-3,5-dichloro-α-[[[6-[2-(6-methyl-2-pyridinyl)ethoxy]hexyl](phenylmethyl)amino]methyl]benzenemethanol From Intermediate 1 (1.5 g) and N-[6-[2-(6-methyl-2-pyridinyl)ethoxy]hexyl]benzenemethanamine (1.6 g), with reaction times of overnight and 2 h for the two stages. FCC eluting with System C (92:8:1) gave the *title compound* as a pale yellow oil (1.7 g), t.l.c. (System C 92:8:1) Rf 0.17.

Intermediate 28

4-Amino-3,5-dichloro-α-[[(phenylmethyl)[6-[3-(4-pyridinyl)propoxy]hexyl]amino]methyl]benzenemethanol From Intermediate 1 (870 mg) and N-[6-[3-(4-pyridinyl)propoxy]hexyl]benzenemethanamine (1.0 g), with reaction times of 3 h and 2 h for the two stages. FCC eluting with System B (60:40:1) gave the *title compound* as a yellow oil (700 mg), t.l.c. (System B 80:20:1) Rf 0.04.

Intermediate 29

4-Amino-3,5-dichloro-α-[[(phenylmethyl)[6-[4-(2-pyridinyl)butoxy]hexyl]amino]methyl]benzenemethanol From Intermediate 1 (1.75 g) and N-[6-[4-(2-pyridinyl)butoxy]hexyl]benzenemethanamine (2.1 g) with reaction times of overnight and 2 h for the two stages. FCC eluting with System B (60:40:1→50:50:1)

gave the *title compound* as a yellow oil (2.7 g), t.l.c. (System B 50:50:1) Rf 0.36.

Intermediate 30

4-Amino-3,5-dichloro-α-[[(phenylmethyl)[5-[2-(2-pyridinyl)ethoxy]pentyl]amino]methyl]benzenemethanol From Intermediate 1 (2.0 g) and N-[5-[2-(2-pyridinyl)ethoxy]pentyl]benzenemethanamine (2.11 g), with reaction times of 24 h and 3 h for the two stages. FCC eluting with diethyl ether-hexane (3:2→4:2) gave the *title compound* as a yellow oil (2.74 g), t.l.c. (System C 95:5:1) Rf 0.27.

Intermediate 31

4-Amino-3,5-dichloro-α-[[(phenylmethyl)[6-[2-(3-pyridinyl)ethoxy]hexyl]amino]methyl]benzenemethanol From Intermediate 1 (2.98 g) and N-[6-[2-(3-pyridinyl)ethoxy]hexyl]benzenemethanamine (3 g), with reaction times of overnight and 3 h for the two stages. FCC eluting with System C (95:5:1) gave the *title compound* as a light brown oil (3 g), t.l.c. (System C 95:5:1) Rf 0.2.

Intermediate 32

4-Amino-3,5-dichloro-α-[[(phenylmethyl)[5-[3-(2-pyridinyl)propoxy]pentyl]amino]methyl]benzenemethanol From Intermediate 1 (2 g) and N-[5-[3-(2-pyridinyl)propoxy]pentyl]benzenemethanamine (2.2 g) with reaction times of overnight and 18 h for the two stages. FCC eluting with System C (95:5:1) gave the *title compound* as a brown oil (2.3 g), t.l.c. (System C 95:5:1) Rf 0.15.

Intermediate 33

(E,Z)-4-[3-(Phenylmethoxy)-2-pyridinyl]-3-buten-1-ol

A mixture of 3-(phenylmethoxy)pyridine-2-carboxaldehyde (3.9 g), (3-hydroxypropyl)triphenylphosphonium bromide (8.38 g) and potassium carbonate (3.3 g) in dioxan (30 ml) containing water (0.27 ml) was heated under reflux for 18 h. The cooled mixture was diluted with ether, filtered and the filtrate was evaporated. The residue was purified by FCC eluting with ether-hexane (3:2)→ether to give the *title compound* as a yellow oil (3.5 g), t.l.c. (ether) Rf 0.23.

Intermediate 34

2-[4-[(6-Bromohexyl)oxy]butyl]-3-hydroxypyridine (Z)-2-[4-[(6-Bromohexyl)oxy]-1-butenyl]-3-(phenylmethoxy)pyridine (1.5 g) was hydrogenated over prereduced 10% palladium oxide on carbon (50% aqueous paste, 300 mg) in ethanol (15 ml). The catalyst was removed by filtration through hyflo and the solvent was evaporated to give the *title compound* as a yellow oil (1.18 g).

Analysis Found: C, 54.51; H, 7.41; N, 4.3; Br, 23.83; $C_{15}H_{14}BrNO_2$ requires C, 54.55; H, 7.32; N, 4.24; Br, 24.19%.

Intermediate 35

6-[3-(2-Pyridinyl)propoxy]-hex-4-yn-1-ol n-Butyl lithium (1.57M in hexane, 35 ml) was added to a stirred solution of 2-[3-[(2-propynyl)oxy]propyl]pyridine (9.0 g) in dry THF (60 ml) at −78° under nitrogen. Boron trifluoride etherate (6.8 ml) was added and the mixture was stirred at −78° for 30 min. Oxetane (10 ml) was added and after 2 h at −78°, the mixture was treated with more oxetane (10 ml). The dark mixture was allowed to warm to 0°, saturated ammonium chloride (100 ml) was added and the mixture was extracted with ethyl acetate (2×50 ml). The organic layer was washed with brine, dried and concentrated to a dark oil which was purified by FCC eluting with ether to give the *title compound* as an orange oil (5.1 g), t.l.c. (ethyl acetate-triethylamine 99:1) Rf 0.35.

Intermediate 36

2-[3-[(6-Bromo-2-hexynyl)oxy]propyl]pyridine

Triphenylphosphine (2.89 g) in dichloromethane (20 ml) was added dropwise to a solution of 6-[3-(2-pyridinyl)propoxy]-4-hexyn-1-ol (2.33 g) and carbon tetrabromide (3.65 g) in dichloromethane (30 ml) cooled in an ice-bath. The reaction mixture was stirred at room temperature for 1 h, the solvent was evaporated and the residue was purified by FCC eluting with hexane-ether (1:1) to give the *title compound* as an orange oil (2.0 g), t.l.c. (hexane-ether 1:1) Rf 0.2.

Intermediate 37

N-[6-[2-(3-pyridinyl)ethoxy]hexyl]benzenemethanamine

A mixture of 3-pyridineethanol (4 g), 1,6-dibromohexane (23.78 g), TAB (0.5 g) and 2N sodium hydroxide (50 ml) was vigorously stirred for 3 h. The mixture was diluted with water (75 ml), extracted with ethyl acetate and the combined organic extracts were washed with brine (150 ml), dried and evaporated. The resulting oil was purified by FCC eluting with hexane→hexane-ethyl acetate (19:1) to give 3-[2-[(6-bromohexyl)oxy]ethyl]pyridine (6 g). A solution of this bromocompound (5 g) and benzylamine (15 ml) was stirred at 140° under nitrogen for 1 h. The cooled reaction mixture was partitioned between sodium bicarbonate (150 ml) and ethyl acetate (50 ml). The organic layer was washed with brine (50 ml), dried and concentrated to give a yellow oil. The excess benzylamine was removed by distillation and the resulting oil was purified by FCC eluting with System C (95:5:1) to give the *title compound* as a yellow oil (4 g), t.l.c. (System A 80:20:1) Rf 0.5.

Intermediate 38

3-(5-Bromo-2-pyridinyl)-2-propyn-1-ol

Copper (I) iodide (10 mg) was added to a solution of 2,5-dibromopyridine (4.74 g), propargyl alcohol (1.34 g) and BTPC (75 mg) in diethylamine (50 ml) and the mixture stirred overnight (18 h), under nitrogen. The solution was evaporated in vacuo and the residue treated with 8% sodium bicarbonate (50 ml) and partitioned with dichloromethane (3×50 ml). The combined extracts were dried and evaporated and the residual semi-solid purified by FCC. Eluting with ether afforded the *title compound* (3.43 g) as fawn crystals m.p. 121°–122°.

Intermediate 39

5-Bromo-2-pyridinepropanol

To a suspension of 3-(5-bromo-2-pyridinyl)-2-propyn-1-ol (0.5 g) and dipotassium azadicarboxylate (3.66 g) in pyridine (40 ml) was added acetic acid (2 ml) and the mixture stirred at room temperature for 24 h, with further additions of acetic acid after 2 h (0.16 ml) and 17 h (2.16 ml). As reduction had only partially gone to completion, further dipotassium azadicarboxylate (3.2 g) and acetic acid (1.86 ml) were added, and stirring continued for 17 h. The mixture was quenched with water (15 ml) and evaporated in vacuo. The residue was co-evaporated with toluene (15 ml) and the residue partitioned between 8% sodium bicarbonate solution (60 ml) and ethyl acetate (60 ml) and the organic phase dried and evaporated in vacuo. The oily residue was purified by FCC using ether and ether-methanol (5%) eluants to afford the *title compound* as a yellow oil (0.42 g).

Analysis Found: C, 44.4; H, 4.9; N, 6.3; $C_8H_{10}BrNO$ requires C, 44.5; H, 4.7; N, 6.5%.

Intermediate 40

4-Amino-3,5-dichloro-α-[[[6-[[3-(3-methoxy-2-pyridinyl)-2-propynyl]oxy]hexyl](phenylmethyl)amino]methyl]benzenemethanol A solution of 2-bromo-3-methoxypyridine (2 g), 4-amino-3,5-dichloro-α-[[(phenylmethyl)[6-[(2-propynyl)oxy]hexyl]amino]methyl]benzenemethanol (5.74 g), BTPC (150 mg), copper (I) iodide (15 mg) in diethylamine (20 ml) and THF (10 ml) was stirred under nitrogen overnight. The solution was concentrated in vacuo to give a brown oil which was purified by FCC eluting with System C (95:5:1) to give the *title compound* as a brown oil (4.6 g), t.l.c. (System A 80:20:1) Rf 0.6.

Intermediate 41

7-[2-(2-Pyridinyl)ethoxy]-2-heptanone

A mixture of 2-[2-[(4-bromobutyl)oxy]ethyl]pyridine (6.2 g), 2,4-pentanedione (3.61 g), potassium carbonate (4.75 g) and potassium iodide (3.95 g) in ethanol (125 ml) was stirred and heated overnight under reflux. The solids were removed by filtration and the filtrate evaporated to leave a dark brown semi-solid. Addition of ether (200 ml) and filtration of the solid produced a brown solution which was evaporated to give a brown oil (4.71 g). Purification by FCC eluting with ether-hexane (1:1→3:1) gave the *title compound* as a pale yellow oil (1.93 g).

Analysis Found: C, 71.11; H, 9.03; N, 5.98; $C_{14}H_{21}NO_2$ requires C, 71.45; H, 9.00; N, 5.95%.

Intermediate 42

6-[2-(2-Pyridinyl)ethoxy]hexanol

A mixture of 2-[2[(6-bromohexyl)oxy]ethyl]pyridine (9.0 g), sodium acetate trihydrate (34.24 g), trictylpropylammonium chloride (1.9 g) and water (25 ml) was stirred under reflux for 2 h. 2N sodium hydroxide solution (50 ml) and ethanol (50 ml) were added to the cooled mixture which was further stirred for 10 min at room temperature. The ethanol was evaporated in vacuo and the residue diluted with brine (150 ml) and extracted with ether (2×100 ml). The combined organic extracts were washed successively with water (150 ml), brine (100 ml), dried and evaporated in vacuo to give a yellow oil. Purification by FCC eluting with ether gave the *title compound* as a colourless oil (4.94 g), t.l.c. (ether) Rf 0.31.

Intermediate 43

6-[2-(2-Pyridinyl)ethoxy]hexanal

A solution of 6-[2-(2-pyridinyl)ethoxy]hexanol (1.0 g) in dichloromethane (8 ml) was added dropwise over 15 min to a stirred suspension of pyridinium chlorochromate (1.83 g) and silica (Merck 7734, 2.9 g) in dichloromethane (30 ml). The mixture was stirred at room temperature under nitrogen for 4 h, diluted with ether (100 ml) and filtered through silica (Merck 9385, 200 ml), eluting with dichloromethane followed by methanol to give a brown oil. Purification by FCC eluting with ether gave the *title compound* as a yellow oil (0.49 g), t.l.c. (System A 40:10:1) Rf 0.42.

Intermediate 44

6-[2-(2-Pyridinyl)ethoxy]hexanoic acid

A solution of 6-[2-(2-pyridinyl)ethoxy]hexanol (1.0 g) and pyridinium dichromate (5.90 g) in DMF (12 ml) was stirred at room temperature for 24 h. The solution was diluted with water (100 ml) and extracted with ether (2×100 ml). The combined organic extracts were washed with water (100 ml), dried and evaporated in vacuo to give a colourless oil. The original aqueous washes were combined and re-extracted with dichloromethane (2×150 ml), washed with water (100 ml), dried and evaporated in vacuo to give a brown oil. The original aqueous washes were then buffered to pH 6.5 using phosphate buffer and solid NaCl added. The saturated solution was extracted with dichloromethane (2×100 ml), washed with water (100 ml), dried and evaporated in vacuo to give a brown oil. The three oils were combined and purified by FCC eluting with hexane-ether (1:1) followed by methanol to afford a yellow oil, which was dissolved in dichloromethane (50 ml) and filtered. The filtrate was evaporated in vacuo to give the *title compound* as a green oil (0.55 g), t.l.c. (System A 40:10:1) Rf 0.6.

Intermediate 45

N-[2-(4-Amino-3,5-dichlorophenyl)-2-hydroxyethyl]-6-[2-(2-pyridinyl)ethoxy]hexanamide 1',1-Carbonyldiimidazole (0.41 g) was added portionwise to a mixture of 6-[2-(2-pyridinyl)ethoxy]hexanoic acid (0.5 g) in acetonitrile (30 ml) at room temperature under nitrogen. The mixture was stirred for 3 h, then a suspension of Intermediate 2 (0.46 g) in acetonitrile (10 ml) was added dropwise at room temperature. The mixture was stirred for 2.5 h at room temperature under nitrogen. The solvent was evaporated in vacuo and the residue purified by FCC eluting with toluene-ethanol-triethylamine-0.88 ammonia (95:5:1:0→40:10:0:1) gave the *title compound* as a colourless oil (0.23 g), t.l.c. (System A 40:10:1) Rf 0.39.

Intermediate 46

α-[[Acetyl[6-[2-(2-pyridinyl)ethoxy]hexyl]amino]methyl]-4-amino-3,5-dichlorobenzenemethanol acetate (ester)

Acetic anhydride (132 mg) in pyridine (2 ml) was added dropwise to a solution of 4-amino-3,5-dichloro-α-[[[6-[2-(2-pyridinyl)ethoxy]hexyl]amino]methyl]benzenemethanol (250 mg) in pyridine (2 ml). The solution was stirred under nitrogen at room temperature overnight and more acetic anhydride (66 mg) in pyridine was added. After stirring for a further 12 h, the solution was evaporated in vacuo to give an oil which was partioned between water (5 ml) and ether (5 ml). The aqueous layer was re-extracted with ether (5 ml) and the combined organic layers were dried and concentrated to give the *title compound* as a clear oil (190 mg), t.l.c. (System A 80:20:1) Rf 0.5.

Intermediate 47

6-[2-(2-Pyridinyl)ethoxy]hexanamine

A solution of N-[6-[2-(2-pyridinyl)ethoxy]hexyl]benzenemethanamine (2.00 g) in ethanol (10 ml) was added to a pre-hydrogenated suspension of 10% palladium on carbon (50% paste, 800 mg) in ethanol (120 ml) and hydrogenated at room temperature and pressure. The catalyst was removed by filtration through hyflo and the solvent evaporated in vacuo. The residual oil was purified by FCC eluting with System A (39:10:1→32:17:1) to afford the *title compound* as a colourless liquid (0.99 g), t.l.c. (System A 39:10:1) Rf 0.16.

Intermediate 48

1-(4-Amino-3,5-dichlorophenyl)-2-[[6-[2-(2-pyridinyl)ethoxy]hexyl]amino]ethanone A mixture of Intermediate 1 (0.51 g), 6-[2-(2-pyridinyl)ethoxy]hexanamine (0.40 g), DEA (0.36 ml) and THF (10 ml) was allowed to stand for 5 h. The mixture was filtered and evaporated in vacuo. The residual gum was purified by FCC eluting with toluene-ethanol (9:1) to afford the *title compound* as a yellow gum (0.45 g), t.l.c. (Toluene: ethanol 9:1) Rf 0.45.

Intermediate 49

5-(4-Amino-3,5-dichlorophenyl)-3-[6-[2-(2-pyridinyl)ethoxy]hexyl]-2-oxazolidinone A solution of the compound of Example 3 (100 mg) and 1,1′-carbonyldiimidazole (38 mg) in dry THF (20 ml) was heated under nitrogen for 5 h. The solvent was evaporated and the residue purified by FCC eluting with ethyl acetate to give the *title compound* as a pale yellow oil (95 mg), t.l.c. (ethyl acetate) Rf 0.42.

Intermediate 50

2-[2-[(6-Bromohexyl)oxy]ethyl]pyridine N-oxide m-Chloroperbenzoic acid (1.13 g) was added in one portion to a solution of 2-[2-[(6-bromohexyl)oxy]ethyl]pyridine (1.0 g) in dichloromethane (50 ml). The solution was stirred at room temperature overnight. The mixture was quenched with 10% w/v sodium sulphite solution (50 ml) and the organic layer washed with 8% sodium bicarbonate solution (50 ml). The organic layer was dried and evaporated to leave the *title compound* as a pale yellow oil (980 mg) used without further purification. A portion (100 mg) was purified by FCC eluting with System A (80:20:1) to give a pale yellow oil (20 mg), t.l.c. (System A 80:20:1) Rf 0.48.

Intermediate 51

4-Amino-3,5-dichloro-α-[[[6-[2-(2-pyridinyl)ethoxy]hexyl]amino]methyl]benzenemethanol 1-oxide (E)-butenedioate salt (4:3)

A solution of Intermediate 2 (0.74 g), 2-[2-[(6-bromohexyl)oxy]ethyl]pyridine N-oxide (0.674 g) and DEA (346 mg) in DMF (15 ml) was heated at 80° for 2 h. The solvent was removed under high vacuum and the residue purified by FCC eluting with System A (90:10:1) to give *the free base of the title compound* as a pale yellow oil (488 mg). A sample of the free base (388 mg) was dissolved in methanol (20 ml) and a solution of fumaric acid (51 mg) in methanol (5 ml) added. The solution was evaporated and the residue triturated under ether (50 ml) to give the *title compound* as a white powder (378 mg), t.l.c. (System A 80:20:1) Rf 0.35.

Analysis Found: C,54.30; H,6.5; N,7.23; Cl,12.65; $C_{21}H_{29}Cl_2N_3O_3.0.75$ $C_4H_4O_4.0.35C_4H_{10}O.0.25H_2O$ requires C,54.78; H,6.0; N,7.55; Cl,12.73%.

EXAMPLE 1

4-Amino-3,5-dichloro-α-[[[6-[3-(2-pyridinyl)propoxy]hexyl]amino]methyl]benzenemethanol A solution of (Z)-4-amino-3,5-dichloro-α-[[(phenylmethyl)[6-[[3-(2-pyridinyl)-2-propenyl]oxy]hexyl]amino]methyl]benzenemethanol (0.65 g) in ethanol (15 ml) containing hydrochloric acid (2.7 mmol) was hydrogenated over 10% palladium on charcoal (0.15 g), filtered and evaporated. The residue was partitioned between aqueous sodium bicarbonate (1M; 30 ml) and ethyl acetate (150 ml) and the dried organic phase was evaporated to give a brown gum. The gum was purified by FCC eluting with System A (93:7:1→85:15:1), to give the *title compound* as a white solid (0.32 g) m.p. 38°–41°.

Analysis Found: C,59.6; H,7.0; N,9.2; $C_{22}H_{31}Cl_2N_3O_2$ requires C,60.0; H,7.1; N,9.5%; (E)-butenedioate (salt) (2:1) m.p. 103°–108°; benzoate (1:1) m.p. 87°–89°; hydrobromide (1:2) m.p. 67°–72°.

EXAMPLE 2

4-Amino-3,5-dichloro-α-[[[6-[3-(3-methoxy-2-pyridinyl)propoxy]hexyl]amino]methyl]benzenemethanol (E)-butenedioate (2:1) (salt)

Following the method of Example 1, 4-amino-3,5-dichloro-α-[[[6-[[3-(3-methoxy-2-pyridinyl)-2-propynyl]oxy]hexyl](phenylmethyl)amino]methyl]benzenemethanol (14.43 g) was hydrogenated over pre-reduced palladium oxide on carbon (50% aqueous paste, 800 mg) in ethanol (40 ml) containing hydrochloric acid (conc. HCl/ethanol; 1:9 v/v, 14.5 ml). The yellow oil obtained after FCC eluting with System C (95:5:1→92:5:1) was dissolved in methanol, treated with fumaric acid (259 mg) and concentrated in vacuo to give a yellow gum which was triturated several times with ether to give the *title compound* as a white solid (2.5 g) m.p. 103°–105°.

Analysis Found: C,56.7; H,6.8; N,7.75; Cl,13.5; $(C_{23}H_{33}Cl_2N_3O_3)_2 \cdot C_4H_4O_4$ requires C,56.82; H,6.68; N,7.95; Cl,13.42%.

EXAMPLE 3

4-Amino-3,5-dichloro-α-[[[6-[2-(2-pyridinyl)ethoxy]hexyl]amino]methyl]benzenemethanol 4-Amino-3,5-dichloro-α-[[(phenylmethyl)[6-[2-(2-pyridinyl)ethoxy]hexyl]amino]methyl]benzenemethanol (1.1 g) was hydrogenated over pre-reduced 10% palladium oxide on carbon (50% aqueous paste, 200 mg) in ethanol (10 ml) containing hydrochloric acid (conc. HCl/ethanol, 1:9 v/v, 4 ml). The catalyst was removed by filtration through hyflo, the solvent was evaporated and the residual oil was partitioned between 8% sodium bicarbonate (25 ml) and ethyl acetate (25 ml). The organic layer was washed with 8% sodium bicarbonate, water and brine, dried and concentrated to an orange oil which was purified by FCC eluting with System C (95:5:1→90:10:1) to give a yellow oil which was triturated with ether-hexane to give the *title compound* as a white solid (280 mg) m.p. 94°–96°.

Analysis Found: C,58.89; H,6.93; N,9.55; Cl,16.88; $C_{21}H_{29}Cl_2N_3O_2$ requires C,59.16; H,6.86; N,9.86; Cl,16.63%.

Examples 4–8 were prepared in a similar manner by hydrogenating the appropriate N-(phenylmethyl)-compound:

EXAMPLE 4

4-Amino-3,5-dichloro-α-[[[6-[2-(6-methyl-2-pyridinyl)ethoxy]hexyl]amino]methyl]benzenemethanol, (E)-butenedioate (salt) (2:1) From 4-amino-3,5-dichloro-α-[[[6-[2-(6-methyl-2-pyridinyl)ethoxy]hexyl](phenylmethyl)amino]methyl]benzenemethanol (1.66 g). FCC eluting with System C (92:8:1) gave a pale yellow oil (0.9 g). A solution of the oil (870 mg) and fumaric acid (126 mg) in methanol (10 ml) was concentrated to an oil which was triturated several times with ether to give the *title compound* as a white solid (850 mg) m.p. 122°–126°.

Analysis Found: C,57.48; H,6.59; N,8.07, Cl,14.18; $(C_{22}H_{31}Cl_2N_3O_2)_2.C_4H_4O_4$ requires: C,57.83; H,6.67; N,8.43; Cl,14.23%.

EXAMPLE 5

4-Amino-3,5-dichloro-α-[[[6-[3-(4-pyridinyl)propoxy]hexyl]amino]methyl]benzenemethanol, (E)-butenedioate(salt)(2:1) From 4-amino-3,5-dichloro-α-[[(phenylmethyl)[6-[3-(4-pyridinyl)propoxy]hexyl]amino]methyl]benzenemethanol (690 mg). Concentration of the ethyl acetate extracts gave a red oil (500 mg). A solution of the oil and fumaric acid (70 mg) in methanol (5 ml) was evaporated to a yellow oil which was triturated several times with ether to give the *title compound* as a cream solid (380 mg), m.p. 112°–115°.

Analysis Found: C,56.49;H,6.52;N,7.89; $(C_{22}H_{31}Cl_2N_3O_2)_2.C_4H_4O_4.0.6H_2O$ requires: C,56.60;H,6.78;N,8.25%.

EXAMPLE 6

4-Amino-3,5-dichloro-α-[[[5-[3-(2-pyridinyl)propoxy]pentyl]amino]methyl]benzenemethanol From 4-amino-3,5-dichloro-α-[[(phenylmethyl)[5-[3-(2-pyridinyl)propoxy]pentyl]amino]methyl]benzenemethanol (2.3 g). FCC eluting with System C (95:5:1) gave the *title compound* as a pale yellow oil (1.6 g), t.l.c. (System C 95:5:1) Rf 0.1. A solution of the title compound (800 mg) and fumaric acid (100 mg) in methanol (10 ml) was concentrated to an oil which was triturated several times with ether to give the (E)-*butenedioate* (salt) (2:1) as a white solid (800 mg) m.p. 135°–137°.

Analysis Found: C,56.80; H,6.49; N,8.30; Cl,14.31; $(C_{21}H_{29}Cl_2N_3O_2)_2.C_4H_4O_4$ requires C,57.03; H,6.45; N,8.67; Cl,14.64%.

EXAMPLE 7

4-Amino-3,5-dichloro-[[[6-[4-(2-pyridinyl)butoxy]hexyl]amino]methyl]benzenemethanol From 4-amino-3,5-dichloro-α-[[(phenylmethyl)[6-[4-(2-pyridinyl)butoxy]hexyl]amino]methyl]benzenemethanol (2.7 g). FCC eluting with System C (95:5:1) gave a yellow oil which solidified on standing to give the *title compound* as a white solid (1.9 g) m.p. 48°–50°, t.l.c. (System C 80:20:2) Rf 0.16. (E)-butenedioate (salt) (2:1) m.p. 107°–108°.

EXAMPLE 8

4-Amino-3,5-dichloro-α-[[[5-[2-(2-pyridinyl)ethoxy]pentyl]amino]methyl]benzenemethanol From 4-amino-3,5-dichloro-α-[[(phenylmethyl)[5-[2-(2-pyridinyl)ethoxy]pentyl]amino]methyl]benzenemethanol (2.67 g), using pre-reduced 10% palladium on charcoal (50% aqueous paste, 400 mg) as the catalyst for hydrogenation. FCC eluting with System C (95:5:1) gave the *title compound* as a pale yellow oil (1.74 g), t.l.c. (System C 95:5:1) Rf 0.07. A solution of the title compound (900 mg) in methanol (5 ml) was treated with fumaric acid (127 mg) in methanol (5 ml) and the solution was concentrated. Trituration of the resultant foam with diethyl ether gave the (E)-*butenedioate* (salt) (2:1) as a white solid (0.95 g), m.p. 140°–142°.

Analysis Found: C,56.1; H,6.4; N,8.7; Cl,14.7; $(C_{20}H_{27}Cl_2N_3O_2)_2.C_4H_4O_4$ requires C,56.2; H,6.2; N,8.9; Cl,15.1%.

EXAMPLE 9

4-Amino-3,5-dichloro-α-[[[6-[3-(3-pyridinyl)propoxy]hexyl]amino]methyl]benzenemethanol (E)-butenedioate (salt)(2:1)

4-Amino-3,5-dichloro-α-[[(phenylmethyl)[6-[3-(3-pyridinyl)propoxy]hexyl]amino]methyl]benzenemethanol (1.5 g) was hydrogenated over pre-reduced 10% palladium on carbon (50% aqueous paste, 300 mg) in ethanol (20 ml) containing hydrochloric acid (conc. HCl/EtOH 1:9, v/v, 5 ml). The catalyst was removed by filtration through hyflo and the solvent was evaporated. The residual oil was partitioned between 8% sodium bicarbonate (50 ml) and ethyl acetate (50 ml) and the organic layer was washed with water and brine, dried and concentrated to an oil which was purified by FCC eluting with System C (95:5:1→90:10:1) to give a slightly coloured oil (850 mg). The oil in methanol (10 ml) was treated with a solution of fumaric acid (115 mg) in methanol (2 ml). The solvent was evaporated and the residue was triturated with dry ether to give the *title compound* as a white powder (770 mg), t.l.c. (System A 80:20:2) Rf 0.40.

Analysis Found: C,57.53; H,6.75; N,8.12; Cl,13.90; $(C_{22}H_{31}Cl_2N_3O_4)_2.C_4H_4O_4$ requires C,57.83; H,6.67; N,8.43; Cl,14.23%.

EXAMPLE 10

4-Amino-3,5-dichloro-α-[[[6-[4-(3-hydroxy-2-pyridinyl)butoxy]hexyl]amino]methyl]benzenemethanol 4-Amino-3,5-dichloro-α-[[[6-[4-(3-hydroxy-2-pyridinyl)butoxy]hexyl](phenylmethyl)amino]methyl]benzenemethanol (0.49 g) was hydrogenated over pre-reduced 10% palladium oxide on carbon (50% aqueous paste, 100 mg) in ethanol (10 ml) containing hydrochloric acid (conc. HCl/ethanol, 1:9 v/v, 1.6 ml). The catalyst was removed by filtration through hyflo, the solvent was evaporated and the residual oil was partitioned between 8% sodium bicarbonate (15 ml) and ethyl acetate (15 ml). The organic layer was washed with 8% sodium bicarbonate (10 ml), water (10 ml) and brine (10 ml), dried and concentrated to a yellow oil which was purified by FCC eluting with System C (95:5:1) to give a pale yellow oil which was triturated with ether to give the *title compound* as a white solid (215 mg) m.p. 95°–96°.

Analysis Found: C,58.32; H,7.38; N,8.7; Cl,15.21; $C_{23}H_{33}Cl_2N_3O_3$ requires C,58.72; H,7.07; N,8.93; Cl,15.07%; (E)-butenedioate (salt) (2:1) m.p. 97°–99°.

EXAMPLE 11

4-Amino-3,5-dichloro-α-[[[6-[2-(3-pyridinyl)ethoxy]-hexyl]amino]methyl]benzenemethanol (E)-butenedioate (salt) (2:1)

4-Amino-3,5-dichloro-α-[[(phenylmethyl)[6-[2-(3-pyridinyl)ethoxy]hexyl]amino]methyl]benzenemethanol (2.98 g) was hydrogenated over pre-reduced 10% palladium oxide on carbon (50% aqueous paste, 800 mg) in ethanol (30 ml) containing hydrochloric acid (conc. HCl/ethanol 1:9 v/v, 10.5 ml). The catalyst was removed by filtration through hyflo, the solvent was evaporated and the residual oil was partitioned between 8% sodium bicarbonate (40 ml) and ethyl acetate (40 ml). The organic layer was washed with sodium bicarbonate (40 ml), water (40 ml) and brine (40 ml) and concentrated to a brown oil which was purified by FCC eluting with System C (95:5:1) to give a yellow oil (1.58 g). A solution of the oil (1.57 g) and fumaric acid (216 mg) in methanol (10 ml) was concentrated to give an oil which was triturated several times in ether to give the *title compound* as a white solid (1.47 g) m.p. 103°–105°.

Analysis Found: C,57.26; H,6.59; N,8.41; Cl,14.29; $(C_{21}H_{29}Cl_2N_3O_2)_2 \cdot C_4H_4O_4$ requires C,57.03; H,6.45; N,8.67; Cl,14.64%.

EXAMPLE 12

4-Amino-3,5-dichloro-α-[[[6-[3-(2-pyridinyl)propoxy]-4-hexynyl]amino]methyl]benzenemethanol, (E)-butenedioate (salt) (2:1)

2-[3-[(6-Bromo-2-hexynyl)oxy]propyl]pyridine (1.0 g) was added to a stirred solution of Intermediate 2 (1.12 g) and DEA (1.0 g) in DMF (12 ml) at 100° under nitrogen. After 1 h, the solvent was evaporated and the residue was partitioned between 8% sodium bicarbonate (25 ml) and ethyl acetate (25 ml). The organic layer was washed with brine, dried and concentrated to an oil which was purified by FCC eluting with System C (95:5:1) to give a pale yellow oil (720 mg). A solution of the oil and fumaric acid (105 mg) in methanol (5 ml) was concentrated in vacuo and the residue was triturated with ether to give the *title compound* as a white powder (670 mg), m.p. 139°–141°.

Analysis Found: C,57.98; H,5.99; N,8.41; Cl,13.85; $(C_{22}H_{27}Cl_2N_3O_2)_2 \cdot C_4H_4O_4$ requires C,58.30; H,5.91; N,8.50; Cl,14.34%.

EXAMPLE 13

4-Amino-3,5-dichloro-α-[[[6-[3-(5-bromo-2-pyridinyl)propoxy]hexyl]amino]methyl]benzenemethanol A solution of Intermediate 2 (1.86 g), 2-[3-[(6-bromohexyl)oxy]propyl]-5-bromopyridine (2.13 g) and DEA (0.865 g) in DMF (15 ml) was stirred at 100° for 2.5 h. The solvent was evaporated in vacuo to give an oil. Purification by FCC eluting with System C (95:5:1) gave a yellow oil, which on standing gave a yellow solid. Trituration with diethyl ether gave the *title compound* as a white solid (1.5 g) m.p. 52°–55°.

Analysis Found: C,50.89; H,5.85; N,7.94; Cl,15.04; Br,13.65; $C_{22}H_{30}BrCl_2N_3O_2$ requires C,50.88; H,5.82; N,8.09; Cl,15.39; Br,13.65%.

EXAMPLE 14

4-Amino-3,5-dichloro-α-[[[1-methyl-6-[2-(2-pyridinyl)ethoxy]hexyl]amino]methyl]benzenemethanol (E)-butenedioate salt (2:1)

A solution of Intermediate 2 (0.5 g) and 7-[2-(2-pyridinyl)ethoxy]-2-heptanone (0.532 g) in ethanol (150 ml) containing a solution of concentrated hydrochloric acid in ethanol (1:9 v/v, 4.1 ml) was hydrogenated over pre-reduced platinum oxide catalyst (5% on carbon, 200 mg). The catalyst was removed by filtration through hyflo and the filtrate evaporated. The resulting oil was partitioned between 8% sodium bicarbonate (20 ml) and ethyl acetate (25 ml). The basic solution was extracted with ethyl acetate (2×25 ml). The combined extracts were dried and evaporated to leave a pale orange oil (650 mg). This was combined with the product (160 ml) from another experiment and purified by FCC eluting with System A (90:10:1→80:20:1) to give the *free base of the title compound* as a pale yellow gum (230 mg), t.l.c. (System B 80:20:1) Rf 0.45. The free base (230 mg) was dissolved in methanol (5 ml) and fumaric acid (30 mg) in methanol (1 ml) added. The solution was evaporated and the residue triturated under ether (20 ml) to give the *title compound* as a white powder (200 mg) m.p. 122°–4°.

Analysis Found: C,57.43; H,6.80; N,8.22; Cl,14.46; $(C_{22}H_{31}Cl_2N_3O_2)_2 \cdot C_4H_4O_4$ requires C,57.83; H,6.67; N,8.43; Cl,14.23%.

EXAMPLE 15

4-Amino-3,5-dichloro-α-[[[6-[2-(2-pyridinyl)ethoxy]-hexyl]amino]methyl]benzenemethanol, α,α-diphenylbenzeneacetate (1:1) (salt)

To a warm solution of the compound of Example 3 (100 mg) in isopropanol (2 ml) was added a warm solution of α,α-diphenylbenzeneacetic acid (67.6 mg) in isopropanol (2 ml). The solution was allowed to cool with stirring for 1 h and the resultant solid was filtered off, washed with isopropanol (1 ml), and dried in vacuo at room temperature to give the *title compound* (128 mg), m.p. 125.5°–126.5°.

Assay Found: C,68.55;H,6.3;N,5.75; $C_{21}H_{29}Cl_2N_3O_2 \cdot C_{20}H_{16}O_2$ requires C,68.9;H,6.35;N,5.9%.

The following salts (Examples 16–25) were prepared by treating 4-amino-3,5-dichloro-α-[[[6-[2-(2-pyridinyl)ethoxy]hexyl]amino]methyl]benzenemethanol (free base) (the compound of Example 3) with the appropriate acid:

EXAMPLE 16

Fumarate (2:1)

Free base (100 mg) and fumaric acid (13.6 mg) gave the *title fumarate* (56.2 mg), m.p. 116°–116.5°. N.m.r. δ(DMSO) 1.25 (4H, m, $2CH_2$), 1.48 (4H, m, $2CH_2$), 2.65–2.9 (4H, m, $2CH_2N$), 2.95 (2H, t, $CH_2$-pyr), 3.38 (2H, t, $CH_2O$), 3.5–4.5 (br, NH, OH, $CO_2H$), 3.71 (2H, t, $OCH_2$), 4.7 (1H, dd, CH), 5.48 (2H, s, $NH_2$), 6.45 (1H, s, CH fumarate), 7.2–7.33 (4H, 2CH aromatic, H-3 and H-5 pyr), 7.72 (1H, dt, H-4 pyr), 8.5 (1H, d, H-6 pyr).

EXAMPLE 17

Succinate (2:1)

Free base (500 mg) and succinic acid (69.2 mg) gave the *title succinate* (320 mg) m.p. 100°–103°.

Assay Found: C,56.5;H,6.7;N,8.45; (C₂₁H₂₉Cl₂N₃O₂)₂.C₄H₆O₄ requires C,56.9;H,6.65;N,8.65%.

EXAMPLE 18

4-Chlorobenzoate (1:1)

Free base (500 mg) and 4-chlorobenzoic acid (183 mg) gave the *title chlorobenzoate* (300 mg), m.p. 85°–86°.
Assay Found: C,57.35;H,5.85;N,7.0; C₂₁H₂₉Cl₂N₃O₂.C₇H₅ClO₂ requires C,57.7;H,5.9;N,7.2%.

EXAMPLE 19

Benzoate (1:1)

Free base (50 mg) and benzoic acid (14.3 mg) gave the *title benzoate* (31 mg) as a white solid, m.p. 115°–117°.
Assay Found: C,61.0;H,6.5;N,7.45; C₂₁H₂₉Cl₂N₃O₂.C₇H₈O₂ requires C,61.3; H,6.45; N,7.65%.

EXAMPLE 20

Benzenesulphonate (1:1)

Free base (50 mg) and benzenesulphonic acid (19 mg) gave the *title benzenesulphonate* as a fawn coloured solid (20 mg), m.p. 110°–110.5°. N.m.r. δ(DMSO) 1.25 (4H, m, 2CH₂), 1.4–1.7 (4H, m, 2CH₂) 2.8–3.2 (4H, m, 2CH₂), 2.95 (2H, t, CH₂-pyr), 3.38 (3H, m, CH₂O), OH), 3.72 (2H, t, OCH₂), 4.78 (1H, br, CH), 5.59 (2H, s, NH₂), 6.12 (1H, br, NH), 7.2–7.4 (7H, m, 2CH aromatic, H-3 and H-5 pyr, H-3, H-4, H-5 benzenesulphonate), 7.6–7.65 (2H, m, H-1 and H-6 benzenesulphonate), 7.72 (1H, dt, H-4 pyr), 8.3–8.7 (1H, br, SO₃H), 8.5 (1H, d, H-6 pyr).

EXAMPLE 21

Sulphate (2:3)

Free base (200 mg) and sulphuric acid (93.8 mg, 98% w/w) gave the *title sulphate* (0.2 g), m.p. 55°–65° (amorphous).
Assay Found: C,44.15;H,5.9;N,6.95; (C₂₁H₂₉Cl₂N₃O₂)₂.(H₂SO₄)₃ requires C,44.0;H,5.6;N,7.3%.

EXAMPLE 22

1-Hydroxy-2-naphthoate (1:1)

Free base (500 mg) and 1-hydroxy-2-naphthoic acid (220 mg) gave the *title hydroxynaphthoate* (700 mg) as a pale brown solid, m.p. 41°–43° (amorphous).
Assay Found: C,62.3;H,6.1;N,6.5; C₂₁H₂₉Cl₂N₃O₂.C₁₁H₈O₃ requires C,62.55;H,6.05;N,6.85%.

EXAMPLE 23

4-Methylbenzenesulphonate (1:1)

Free base (50 mg) and p-toluenesulphonic acid (22 mg) gave the *title 4-methylbenzenesulphonate* as a cream solid (60 mg), m.p. 128°–130°. N.m.r. δ(DMSO) 1.25 (4H, m, 2CH₂), 1.4–1.7 (4H, m, 2CH₂), 2.31 (3H, s, CH₃), 2.8–3.15 (4H, m, 2CH₂), 2.95 (2H, t, CH₂-pyr), 3.38 (3H, m, CH₂O, OH), 3.71 (2H, t, OCH₂), 4.75 (1H, d, H), 5.59 (2H, s, NH₂), 6.12 (1H, br, NH), 7.13 (2H, d, H-3 and H-5 benzenesulphonate), 7.2–7.35 (4H, m, 2CH aromatic, H-3 and H-5 pyr), 7.5 (2H, d, H-2 and H-6 benzenesulphonate), 7.72 (1H, dt, H-4 pyr), 8.2–8.7 (1H, br, SO₃H), 8.5 (1H, d, H-6 pyr).

EXAMPLE 24

α-Phenylbenzeneacetate (1:1)

Free base (50 mg) and α-phenylbenzeneacetic acid (25 mg) gave the *title α-phenylbenzeneacetate* as a cream solid (46 mg), m.p. 105°–107°. N.m.r. δ(DMSO) 1.24 (4H, m, 2CH₂), 1.45 (4H, m, 2CH₂), 2.6–2.9 (4H, m, 2CH₂), 2.95 (2H, t, CH₂-pyr), 3.37 (2H, t, CH₂O), 3.71 (2H, t, OCH₂), 4.67 (1H, dd, CH), 4.9 (1H, s, CH phenylbenzeneacetate), 5.45 (2H, s, NH₂), 7.15–7.4 (14H, m, 2CH aromatic, H-3, H-5 pyr, 10H phenylbenzeneacetate), 7.7 (1H, dt, H-4 pyr), 8.49 (1H, d, H-6 pyr).

EXAMPLE 25

Adipate (2:1)

Free base (100 mg) and adipic acid (17.1 mg) gave the *title adipate* (54 mg), m.p. 94°–96°.
Assay Found: C,57.25;H,7.05;N,8.35; (C₂₁H₂₉Cl₂N₃O₂)₂.C₆H₁₀O₄ requires C,57.7;H,6.85;N,8.4%.

Example 26

4-Amino-3,5-dichloro-α-[[[6-[2-(2-pyridinyl)ethoxy]-hexyl]amino]methyl]-benzenemethanol A mixture of Intermediate 2 (1.0 g), 2-[2-[(6-bromohexyl)oxy]ethyl]pyridine (0.863 g), DEA (0.66 ml) and DMF (25 ml) was stirred at 100° for 2.5 h. The solvent was evaporated and the residue purified by FCC eluting with System C (95:5:1) to give a colourless oil (0.3 g). A portion was crystallized from ethyl acetate/hexane to give the *title compound* as a white solid m.p. 96°–97°, t.l.c. (System A 39:10:1) Rf 0.44.

EXAMPLE 27

4-Amino-3,5-dichloro-α-[[[6-[2-(2-pyridinyl)ethoxy]-hexyl]amino]methyl]benzenemethanol A solution of Intermediate 2 (0.4 g) and 6-[2-(2-pyridinyl)ethoxy]hexanal (0.4 g) in absolute ethanol (10 ml) containing hydrochloric acid (conc. HCl/ethanol 1:9 v/v, 1.64 ml) was hydrogenated at room temperature over 5% platinum oxide on charcoal catalyst (100 mg) in ethanol (5 ml). The mixture was filtered through hyflo and evaporated in vacuo to give a brown oil. Purification by FCC eluting with System C (95:5:1) gave a colourless oil, which on trituration with hexane gave the *title compound* as a white solid (0.115 g) m.p. 93.5°–95°, t.l.c. (System A 39:10:1) Rf 0.44.

EXAMPLE 28

4-Amino-3,5-dichloro-α-[[[6-[2-(2-pyridinyl)ethoxy]-hexyl]amino]methyl]benzenemethanol A solution of N-[2-(4-amino-3,5-dichlorophenyl)-2-hydroxyethyl]-6-[2-(2-pyridinyl)ethoxy]hexanamide (0.166 g) in benzene (5 ml) was added dropwise to a stirred suspension of lithium aluminium hydride (0.065 g) in ether (5 ml) at room temperature under nitrogen. The mixture was stirred at room temperature under nitrogen for 3 days and then carefully quenched successively with water (0.5 ml), 2N sodium hydroxide (0.5 ml) and water (2 ml). The mixture was diluted with ether (50 ml), filtered through hyflo (washing with additional dichloromethane) and evaporated in vacuo to give an oil. Purification by FCC eluting with System C (95:5:1→90:10:1) gave a colourless oil, which on trituration with ether-hexane gave a white solid (67 mg). Repurification by a further 2 columns on silica (Merck 9385) and triethylamine deactivated silica (Merck 9385, 10 ml) eluting with System C (98:2:1→95:5:1) and toluene-ethanol (98:2) respectively gave a colourless oil which was identified by t.l.c. (System A 39:10:1) Rf 0.44 as the *title compound*.

EXAMPLE 29

4-Amino-3,5-dichloro-α-[[[6-[2-(2-pyridinyl)ethoxy]-hexyl]amino]methyl]benzenemethanol A mixture of α-[[acetyl[6-[2-(2-pyridinyl)ethoxy]hexyl]amino]methyl]-4-amino-3,5-dichlorobenzenemethanol acetate (ester) (130 mg) in sodium hydroxide (5 ml) and ethanol (5 ml) was stirred at room temperature for 18 h. The mixture was heated under reflux for 20 h, cooled, evaporated in vacuo and the aqueous layer extracted with ethyl acetate (2×20 ml). The combined organic extracts were dried and concentrated to give a yellow oil which was triturated in ether/hexane to give the *title compound* as a white solid (80 mg) m.p. 92°-95°, t.l.c. (System A 80:20:1) Rf 0.44.

EXAMPLE 30

4-Amino-3,5-dichloro-α-[[[6-[2-(2-pyridinyl)ethoxy]-hexyl]amino]methyl]benzenemethanol 4-Amino-3,5-dichloro-α-oxobenzeneacetaldehyde (0.56 g) and 6-[2-(2-pyridinyl)ethoxy]hexanamine (0.40 g) were dissolved in benzene (10 ml) and heated under reflux for 1 h using a Dean-Stark water trap. The solution was cooled, evaporated in vacuo and the residue dissolved in methanol (10 ml). Sodium borohydride (0.38 g) was added portionwise at 0°-5° over 0.5 h with stirring. The solution was allowed to stand overnight then evaporated in vacuo. The residue was partitioned between water (50 ml) containing 2N sodium carbonate (4 ml) and ethyl acetate (60 ml). The organic phase was dried, evaporated in vacuo and the residue purified by FCC eluting with System C (90:10:1) to afford a gum. Trituration with hexane gave the *title compound* (85 mg) as a colourless powder m.p. 93°-96°, t.l.c. (System A 39:10:1) Rf 0.44.

EXAMPLE 31

4-Amino-3,5-dichloro-α-[[[6-[2-(2-pyridinyl)ethoxy]-hexyl]amino]methyl]benzenemethanol A solution of 4-amino-3,5-dichloro-α-[[[6-[2-(2-pyridinyl)ethoxy]hexyl]amino]methyl]benzenemethanol 1-oxide (100 mg) in methanol (10 ml) was hydrogenated over Raney nickel catalyst (ca. 100 mg) and the reaction stopped after one mole of hydrogen had been adsorbed (5 ml). The catalyst was removed by filtration through hyflo and the filtrate evaporated to leave a pale pink gum. Purification by FCC eluting with System A (80:20:1) gave the *title compound* as a white crystalline solid (20 mg), m.p. 94°-95°, t.l.c. (System A 39:10:1) Rf 0.44.

EXAMPLE 32

4-Amino-3,5-dichloro-α-[[[6-[2-(2-pyridinyl)ethoxy]-hexyl]amino]methyl]benzenemethanol Sodium borohydride (0.16 g) was added portionwise over 5 min to a solution of 1-(4-amino-3,5-dichlorophenyl)-2-[[6-[2-(2-pyridinyl)ethoxy]hexyl]amino]ethanone (0.44 g) in methanol (7 ml) at 0°-5° with stirring. After 1.5 h, the solution was evaporated in vacuo and the residue partitioned between water (60 ml) and ethyl acetate (100 ml). The organic phase was dried and evaporated in vacuo to a gum which was purified by FCC eluting with System C (90:10:1) to afford a product, which was triturated with hexane (2 ml) to give the *title compound* as a colourless powder (47 mg), m.p. 94.5°-96.5°, t.l.c. (System A 39:10:1) Rf 0.44.

EXAMPLE 33

4-Amino-3,5-dichloro-α-[[[6-[2-(2-pyridinyl)ethoxy]-hexyl]amino]methyl]benzenemethanol.

A solution of 5-(4-amino-3,5-dichlorophenyl)-3-[6-[2-(2-pyridinyl) ethoxy]hexyl]-2-oxazolidinone (80 mg) and 2N hydrochloric acid (1 ml) in THF (5 ml) was heated at 80° for 2 h. The solvent was evaporated and the aqueous residue extracted with ethyl acetate (2×25 ml). The aqueous layer was basified with 2N sodium hydroxide solution to pH10 and extracted with ethyl acetate (3×25 ml). The combined extracts were dried and evaporated to leave a pale yellow gum (70 mg). Crystallisation from ethyl acetate/n-hexane gave the *title compound* as a white crystalline solid m.p. 97.5°-100°, t.l.c. (System A 39:10:1) Rf 0.44.

The following are examples of suitable formulations of compounds of the invention. The term 'active ingredient' is used herein to represent a compound of the invention and may be, for example, the compound of Example 3.

Tablets

These may be prepared by normal methods such as wet granulation or direct compression.

| A. Direct Compression | mg/tablet |
| --- | --- |
| Active Ingredient | 2.0 |
| Microcrystalline Cellulose USP | 196.5 |
| Magnesium Stearate BP | 1.5 |
| Compression Weight | 200.0 |

The active ingredient is sieved through a suitable sieve, blended with the excipients and compressed using 7 mm diameter punches.

Tablets of other strengths may be prepared by altering the ratio of active ingredient to microcrystalline celluose or the compression weight and using punches to suit.

| B. Wet Granulation | mg/tablet |
| --- | --- |
| Active ingredient | 2.0 |
| Lactoss BP | 151.5 |
| Starch BP | 30.0 |
| Pregelatinised Maize Starch BP | 15.0 |
| Magnesium Stearate BP | 1.5 |
| Compression | 200.0 |

The active ingredient is sieved through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

| C. For Buccal administration | mg/tablet |
|---|---|
| Active ingredient | 2.0 |
| Lactose BP | 94.8 |
| Sucrose BP | 86.7 |
| Hydroxypropylmethylcellulose | 15.0 |
| Magnesium Stearate BP | 1.5 |
| Compression Weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film coated with suitable film forming materials, such as hydroxypropylmethylcellulose, using standard techniques. Alternatively the tablets may be sugar coated.

| Capsules | mg/capsule |
|---|---|
| Active ingredient | 2.0 |
| *Starch 1500 | 97.0 |
| Magnesium Stearate BP | 1.0 |
| Fill Weight | 100.0 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

Syrup

This may be either a sucrose or sucrose-free presentation.

| A. Sucrose Syrup | mg/5 ml dose |
|---|---|
| Active Ingredient | 2.0 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredient, buffer, flavour, colour and preservative are dissolved in some of the water and glycerine is added. The remainder of the water is heated to dissolve the sucrose and is then cooled. The two solution are combined, adjusted to volume and mixed. The syrup produced is clarified by filtration.

| B. Sucrose-free | mg/5 ml dose |
|---|---|
| Active ingredient | 2.0 mg |
| Hydroxypropyl methylcellulose USP (Viscosity type 4000) | 22.5 mg |
| Buffer | |
| Flavour | |
| Colour | as required |
| Preservative | |
| Sweetener | |
| Purified Water BP to | 5.0 ml |

The hydroxypropyl methylcellulose is dispersed in hot water, cooled and then mixed with an aqueous solution containing the active ingredient and the other components of the formulation. The resultant solution is adjusted to volume and mixed. The syrup is clarified by filtration.

| Metered Dose Pressurised Aerosol | | |
|---|---|---|
| A. Suspension Aerosol | mg/metered dose | Per can |
| Active ingredient micronised | 0.100 | 26.40 mg |
| Oleic Acid BP | 0.010 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°–15° C. and the micronised drug is mixed into the solution with a high shear mixer. The suspension is metered into aluminium aerosol cans and suitable metering valves delivering 85 mg of suspension are crimped onto the cans and the dichlorodifluoromethane is pressure filled into the cans through the valves.

| B. Solution Aerosol | mg/metered dose | Per can |
|---|---|---|
| Active ingredient | 0.055 | 13.20 mg |
| Ethanol BP | 11.100 | 2.66 g |
| Dichlorotetrafluoroethane BP | 25.160 | 6.04 g |
| Dichlorodifluoromethane BP | 37.740 | 9.06 g |

Oleic acid BP, or a suitable surfactant e.g. Span 85 (sorbitan trioleate) may also be included.

The active ingredient is dissolved in the ethanol together with the oleic acid or surfactant if used. The alcoholic solution is metered into suitable aerosol containers followed by the dichlorotetrafluoroethane. Suitable metering valves are crimped onto the containers and dichlorodifluoromethane is pressure filled into them through the valves.

| Injection for Intravenous Administration | mg/ml |
|---|---|
| Active ingredient | 0.5 mg |
| Sodium chloride BP | as required |
| Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

| Inhalation Cartridges | mg/cartridge |
|---|---|
| Active ingredient micronised | 0.200 |
| Lactose BP to | 25.0 |

The active ingredient is micronised in a fluid energy mill to a fine particular size range prior to blending with normal tabletting grade lactose in a high energy mixer.

The powder blend is filled into No. 3 hard gelatin capsules on a suitable encapsulating machine. The contents of the cartridges are administered using a powder inhaler such as the Glaxo Rotahaler.

|  Suppositories |  |
| --- | --- |
| Active ingredient | 2.0 mg |
| *Witepsol H15 | 1.0 g |

*A proprietary grade of Adeps Solidus Ph. Eur.

A suspension of the active ingredient in molten Witepsol is prepared and filled, using suitable machinery, into 1 g size suppository moulds.

I claim:

1. A compound of formula (I)

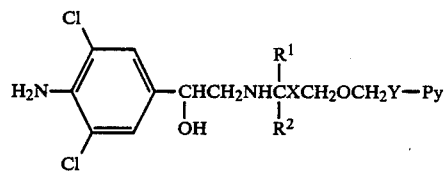

wherein

X represents a bond or a $C_{1-6}$ alkylene, $C_{2-6}$ alkenylene or $C_{2-6}$ alkynylene chain, and Y represents a bond, or a $C_{1-4}$ alkylene, $C_{2-4}$ alkenylene or $C_{2-4}$ alkynylene chain with the proviso that the sum total of carbon atoms in X and Y is not more than 8;

Py represents a pyridyl group optionally substituted by one or two substituents selected from halogen atoms, hydroxy, $C_{1-3}$ alkyl and $C_{1-3}$ alkoxy groups; and $R^1$ and $R^2$ each represent a hydrogen atom or a $C_{1-3}$ alkyl group, with the proviso that the sum total of carbon atoms in $R^1$ and $R^2$ is not more than 4;

or a physiologically acceptable salt or solvate thereof.

2. A compound according to claim 1 in which the sum total of carbon atoms in the chains —X— and —Y— is 4, 5, 6, or 7.

3. A compound according to claim 1 in which —X— is —(CH$_2$)$_3$—, —(CH$_2$)$_4$— or —(CH$_2$)$_2$C≡C— and Y is —CH$_2$—, —(CH$_2$)$_2$— or —(CH$_2$)$_3$—.

4. A compound according to claim 1 in which $R^1$ and $R^2$ are both hydrogen atoms or $R^1$ is a hydrogen atom and $R^2$ is a $C_{1-3}$ alkyl group.

5. A compound according to claim 1 in which the group Py is attached to the rest of the molecule at the 2-, 3- or 4- position and is an unsubstituted pyridyl group or a pyridyl group substituted by a single substituent.

6. A compound of formula (I)

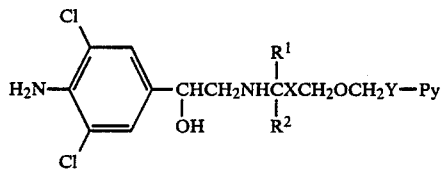

wherein

X represents —(CH$_2$)$_4$— or —(CH$_2$)$_2$C≡C—;

Y represents —CH$_2$—, —(CH$_2$)$_2$— or —(CH$_2$)$_3$—;

$R^1$ represents a hydrogen atom;

$R^2$ represents a hydrogen atom or a methyl group; and

Py represents a pyridyl group attached to the rest of the molecule at the 2-, 3- or 4- position and optionally containing a single substituent selected from hydroxy and methyl;

or physiologically acceptable salt or solvate thereof.

7. A compound according to claim 6 in which $R^1$ and $R^2$ both represent hydrogen atoms; X represents —(CH$_2$)$_4$—; Y represents —CH$_2$—, —(CH$_2$)$_2$— or —(CH$_2$)$_3$—; and Py represents an unsubstituted pyridyl group attached to the rest of the molecule at the 2- or 3- position, or a 2- pyridyl group containing a single hydroxy substituent.

8. A compound according to claim 7 in which Py is an unsubstituted pyridyl group attached to the rest of the molecule at the 2- position.

9. 4-amino-3,5-dichloro-α-[[[6-[2-(2-pyridinyl)ethoxy]hexyl]amino]methyl]benzenemethanol;

and physiologically acceptable salts and solvates thereof.

10. A compound selected from:

4-amino-3,5-dichloro-α-[[[6-[3-(3-pyridinyl)propoxy]hexyl]amino]methyl]benzenemethanol;

4-amino-3,5-dichloro-α-[[[6-[4-(3-hydroxy-2-pyridinyl)butoxy]]hexyl]amino]methyl]benzenemethanol;

4-amino-3,5-dichloro-α-[[[6-[3-(2-pyridinyl)propoxy]hexyl]amino]methyl]benzenemethanol;

4-amino-3,5-dichloro-α-[[[6-[2-(3-pyridinyl)ethoxy]hexyl]amino]methyl]benzenemethanol;

4-amino-3,5-dichloro-α-[[[1-methyl-6-[2-(2-pyridinyl)ethoxy]hexyl]amino]methyl]benzenemethanol;

and physiologically acceptable salts and solvates thereof.

11. A pharmaceutical composition for therapy or prophylaxis of a disease associated with reversible airways obstruction such as asthma or chronic bronchitis, which comprises an effective amount to alleviate said disease of least one compound of formula

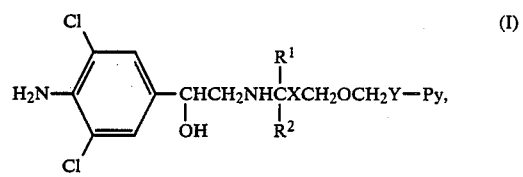

wherein

X represents a bond or a $C_{1-6}$alkylene, $C_{2-6}$alkenylene or $C_{2-6}$alkynylene chain, and Y represents a bond, or a $C_{1-4}$alkylene, $C_{2-4}$alkenylene or $C_{2-4}$alkynylene chain with the proviso that the sum total of carbon atoms in X and Y is not more than 8;

Py represents a pyridyl group optionally substituted by one or two substituents selected from halogen atoms, hydroxy, $C_{1-3}$alkyl and $C_{1-3}$alkoxy groups; and $R^1$ and $R^2$ each represent a hydrogen atom or a $C_{1-3}$alkyl group, with the proviso that the sum total of carbon atoms in $R^1$ and $R^2$ is not more than 4; or a physioloically acceptable salt or solvate thereof, together with a physiologically acceptable carrier or excipient.

12. A method of therapy or prophylaxis of a disease associated with reversible airways obstruction such as asthma or chronic bronchitis in a patient which comprises administering to said patient an effective amount to allevi, said disease of at lease one compound of formula

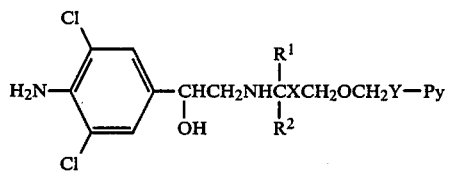

wherein

X represents a bond or a $C_{1-6}$alkylene, $C_{2-6}$alkenylene or $C_{2-6}$alkynylene chain, and Y represents a bond, or a $C_{1-4}$alkylene, $C_{2-4}$alkenylene or $C_{2-4}$alkynylene chain with the proviso that the sum total of carbon atoms in X and Y is not more than 8;

Py represents a pyridyl group optionally substituted by one or two substituents selected from halogen atoms, hydroxy, $C_{1-3}$alkyl and $C_{1-3}$alkoxy groups; and $R^1$ and $R^2$ each represent a hydrogen atom or a $C_{1-3}$alkyl group, with the proviso that the sum total of carbon atoms in $R^1$ and $R^2$ is not more than 4; or a physiologically acceptable salt or solvate thereof.

* * * * *